United States Patent [19]
Demirjian et al.

[11] Patent Number: 5,981,177
[45] Date of Patent: Nov. 9, 1999

[54] PROTEIN FUSION METHOD AND CONSTRUCTS

[76] Inventors: David C. Demirjian, 5050 S. Lakeshore Dr. #1701-S; Malcolm J. Casadaban, 5227 S. Kimbark, both of Chicago, Ill. 60615; J. Mark Weber, 3100 N. Lakeshore Dr. #2103, Chicago, Ill. 60657; George L. Gaines, III, 102 Gale Ave., River Forest, Ill. 60305

[21] Appl. No.: 08/378,548

[22] Filed: Jan. 25, 1995

[51] Int. Cl.$^6$ .............................. C12Q 1/68; C12N 1/21; C12N 15/00
[52] U.S. Cl. ................ 435/6; 435/172.3; 435/252.33; 435/320.1; 536/23.1
[58] Field of Search .......................... 435/172.3, 320.1, 435/69.1, 6, 252.33; 536/24.1, 23.1; 935/10, 44, 47

[56] References Cited

PUBLICATIONS

New England Biolabs catalog, pp. 116–117, 1993.
Manoil, Analysis of Protein Localization by Use of Gene Fusions with Complementary Properties, J. Bacteriol. 172(2): 1035–1042, Feb. 1990.
Clark et al., Transcription of the *Escherichia coli* recE gene from a promoter in Tn5 and IS50, J. Biol. Chem. 176(22): 7024–7031, Oct. 1994.
Camilli et al., Insertional Mutagenesis of Listeria monocytogenes with a novel Tn917 Derivative that allows direct cloning of DNA flanking transposon insertions, J. Bacteriol. 172(7): 3738–3744, Jul. 1990.

Bhagwat et al., Prinary sequence of the EcoRII endonuclease and properties of its fusions with Beta–galactosidase, J. Biol. Chem. 265(2): 767–773, Jan. 1990.

*Phage Mu* edited by N. Symonds, A. Toussaint, P. van de Putte, and M. Howe (Cold Spring Harbor Laboratory, 1987). Chapter 2.

*Phage Mu* edited by N. Symonds, A. Toussaint, P. van de Putte, and M. Howe (Cold Spring Harbor Laboratory, 1987). Chapter 12.

*Phage Mu* edited by N. Symonds, A. Toussaint, P. van de Putte, and M. Howe (Cold Spring Harbor Laboratory, 1987). Chapter 14.

*Primary Examiner*—James Ketter
*Assistant Examiner*—Irem Yucel
*Attorney, Agent, or Firm*—McDonnell Boehnen Hulbert & Berghoff

[57] ABSTRACT

The instant disclosure teaches transposons and methods of the instant invention for making Protein Fusions by rapid, random shuffling of protein domains to produce novel protein fusions. This system is generally applicable to production of multifunctional chimeric proteins in vivo and in vitro. The methods and constructs of the instant invention can be used to randomly create both carboxy- and amino-terminal protein fusions in vivo. The methods and contructs of the instant invention are useful in the development of a protein domain library, in the construction of multifunctional enzymes, and in the accelerated evolution of new enzymatic activities.

19 Claims, 16 Drawing Sheets

```
pIVP315:  Kpn1\  /Nde1                              /Xma3  /Pvu1
          EcoR1\     /BamH1    /Sal1    /Cla1 /Not1       /Nru1  ORF
        GGAATTGGTACCCATATGGAATTCGGATCCGTCGATCGATGCGGCCGCGATCGACAATTCCGT..
rf 1     G  I  G  T  H  M  E  F  G  S  V  D  I  D  A  A  A  D  R  D  N  S  V     -->
rf 2      E  L  V  P  I  W  N  S  D  P  S  T  S  M  R  P  P  I  A  T  I  P  F    XXX
rf 3       N  W  Y  P  Y  G  I  R  I  R  R  H  R  C  G  R  R  S  R  Q  F  R      -->
                  ------------------------------------------------------
rf 4       I  P  V  W  I  S  N  P  D  T  S  M  S  A  A  A  S  R  S  L  E  T      XXX
rf 5      F  Q  Y  G  Y  P  I  R  I  R  R  C  R  H  P  R  R  D  R  C  N  R       XXX
rf 6     S  N  T  G  M  H  F  E  S  G  D  V  D  I  R  G  G  I  A  V  I  G        <--
```

Polylinker sequence:

<u>EcoR I</u>     <u>KpnI</u>     <u>BamH I</u>         <u>PstI</u>
GAATTC<u>GAGCTC</u>GGTA<u>CCCGGG</u>GATCC<u>GTCGAC</u>CTGCAG<u>AAGCTT</u>
      SacI     SmaI       SalI      HindIII

Figure 12
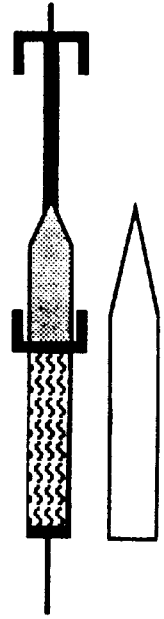
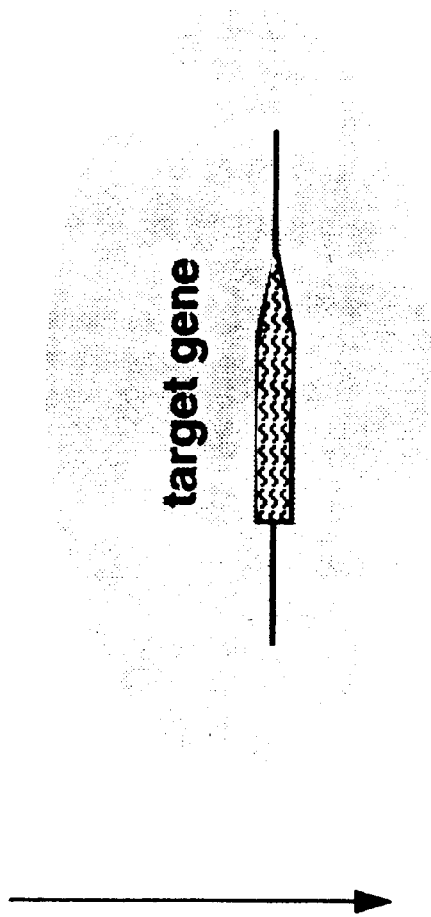
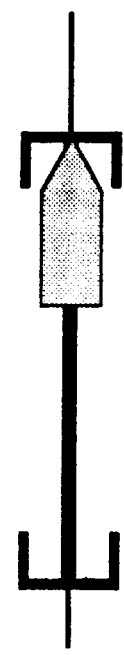
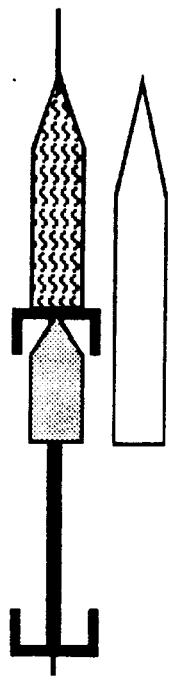

Figure 13

5'-ggggGGTACCgcccgcctaatgagcgggcttttttttCCGACACCATCGAATGGCGCAAAACCTTTC-3'  MALPI-L 5'-ggggGATCCATAATCTATGGTCCTTGTTGGTGAAGTGC-3'  MALPI-R

Figure 14 A

```
        |   10       |   20       |   30          |   40       |   50       |   60
   1 TGTATTGATT CACTTGAAGT ACGAAAAAAA    CCGGGAGGAC ATTGGATTAT TCGGGATCTG   60
  61 ATGGGATTAG ATTTGGTGGG GCTTGCAAGC    CTGTAGTGCA AATTTTAGTC GTTAATCAAT  120
 121 GAAACGCGAA AGATAGTAAA AAATTGCTTT    TGTTTCATTG AAAATACGAA AAACAAAAAC  180
 181 ACTGCAAATC ATTTCAATAA CAGCTTCAAA    AAACGTTCAA AACCGATAAC AACCAAGCTG  240
 241 TCACCAAATG ACTCATATCA CAAATCAGCT    TATGCCGTTT AGGTATGTTA CATGTGTGAT  300
 301 TATGTGAGGT GAAGTATGTT TTAGCTGGTT    CATGGTTGTT ATACGGCTTT TTTTACCTCC  360
 361 GTGGGTTCCT GTGAAGGTAC TACAACACCT    TCCTGTTCAT GAATCCCATA CTTTGACAAA  420
 421 ATCTCTTTGC GTTTTCTTC AGGTAATGCA      TCTAGCATCA TCAACGTCTG AATACTTTGC  480
 481 TGTGAAAATC CTATAAAGCT GTAAAGTTTC    TGTTCATTAA ATACAAGAGG CATTAACGCC  540
 541 AACAACCCCC CTTTACTTAA AAGTTTCAGT    GCCTTGCGTG CTTCATCTGG TTCCAGCTCT  600
 601 TCAATCATAT TGATTAAGGT TGTGGTTAAT    TTGTTTATCA GTTCCGAAGA ATCCTGTTTC  660
 661 TCATTGGCTT GAGCACCAGT ATCCGGTGTG    GATAACCCCA AGTGCGCAAT AACTTGCTCT  720
 721 CGTTCTTTGG TGGGCATCGA CATCACATCG    TATTCAACAG CTTTCCCCCC CTTGACACCT  780
 781 TCCTTTTTTT GCTTCGTCCA GCCTTGAACA    TTTGCTCGAT AGTGAACACC AGCAACAGAT  840
 841 CCAGGCATAC CATCAGCAGC CATAATTTCT    TGCGGCGAAC ACCAAATTGA CTTTTCAGTA  900
 901 TTATTCTTTT CTATAAAGTT ACTTTTCAAA    ATTTAAACTC CTTATTTATC AACGCGTTAA  960
 961 TCAGTAATCA AAGGAATTTA CCAAAAAGCA    GCTTTACATT AAGCTTTTCA GTAATTATCT 1020
1021 TTTTAGTAAG CTAGCTAAGT TTTTACACTT    AGTTAAATTG CTAACTTTAT AGATTACAAA 1080
1081 ACTTAGGAGG GTTTTTAAAT GTGTTCCAAC    GAAAAGGCCC GTGATTGGCA TCGTGCGGAT 1140
1141 GTGATTGCGG GACTTAAGAA AAGAAAGCTC    TCTTTATCAG CTCTTTCCCG GCAGTTTGGT 1200
1201 TATGCGCCAA CTACATTAGC TAATGCGCTA    GAACGACACT GGCCAAAGGG TGAGCAGATT 1260
1261 ATTGCTAACG CCTTAGAAAC TAAACCGGAA    GTAATCTGGC CTAGCCGATA TCAAGCAGGT 1320
1321 GAATAACATG GAACTTTGGG TATCACCGAA    AGAGTGTGCG AATCTTCCTG GTTTGCCGAA 1380
1381 AACATCGGCT GGTGTGATTT ATGTTGCTAA    AAAGCAAGGA TGGCAAAACC GCACTAGAGC 1440
1441 AGGTGTCAAA GGTGGTAAAG CAATTGAATA    CAATGCGAAC TCTTTACCTG TTGAAGCGAA 1500
1501 AGCGGCGTTA TTGCTGAGAC AAGGAGAGAT    TGAAACAAGC CTGGGGTATT TTGAAATCGC 1560
1561 CCGCCCCACG CTGGAAGCCC ATGATTATGA    TCGTGAGGCA CTGTGGAGCA AATGGGATAA 1620
1621 CGCCAGCGAT TCCCAGCGCA GACTTGCTGA    AAAATGGTTG CCTGCGGTTC AGGCTGCAGA 1680
1681 CGAAATGCTG AACCAGGGGA TTTCAACGAA    AACGGCTTTT GCGACCGTTG CAGGGCATTA 1740
1741 CCAGGTCAGC GCATCCACTT TGCGGGACAA    GTATTACCAG GTACAGAAGT TTGCGAAGCC 1800
1801 TGACTGGGCG GCTGCACTTG TTGATGGACG    TGGAGCATCC CGTCGCAATG TTCACAAAAG 1860
1861 TGAATTTGAC GAGGATGCCT GGCAGTTTCT    GATTGCAGAT TATCTGCGAC CGGAAAAACC 1920
1921 CGCTTTCCGC AAATGTTATG AGCGTCTGGA    ACTGGCAGCC CGCGAGCATG GCTGGAGTAT 1980
1981 TCCCTCCCGT GCCACGGCCT TTCGCCGGAT    TCAGCAACTG GACGAGGCAA TGGTTGTTGC 2040
2041 CTGTCGTGAA GGTGAACATG CACTGATGCA    TCTGATACCG GCACAGCAGC GAACTGTGGA 2100
2101 ACACCTGGAC GCCATGCAGT GGATCAACGG    CGACGGTTAT CTGCATAACG TCTTTGTACG 2160
2161 CTGGTTTAAC GGTGATGTGA TCCGTCCGAA    AACATGGTTC TGGCAGGATG TGAAAACCCG 2220
2221 AAAAATTCTG GGCTGGCGCT GCGATGTGAG    CGAGAACATT GATTCAATTC GCCTCTCGTT 2280
2281 CATGGATGTT GTGACTCGCT ACGGTATCCC    GGAGGATTTT CACATCACCA TTGATAACAC 2340
2341 CCGTGGTGCT GCGAATAAAT GGCTGACGGG    AGGCGCGCCC AATCGCTACC GCTTTAAGGT 2400
2401 AAAAGAGGAC GATCCAAAAG GACTGTTTTT    ACTGATGGGG GCGAAAATGC ACTGGACAAG 2460
2461 CGTTGTTGCC GGTAAAGGCT GGGGCCAGGC    AAAACCTGTT GAACGTGCTT TCGGTGTTGG 2520
2521 TGGGCTTGAG GAATACGTTG ATAAGCATTC    GGCACTGGCT GGCGCATATA CGGGGCCAAA 2580
2581 TCCGCAGGCA AAACCTGATA ACTATGGCGA    CCGCGCTGTT GATGCAGAGC TGTTTCTGAA 2640
2641 AACCCTTGCC GAAGGTGTGG CGATGTTCAA    TGCCAGAACA GGCCGTGAAA CAGAAATGTG 2700
2701 CGGGGGCAAA CTCTCGTTTG ATGATGTTTT    CGAGCGTGAA TACGCCAGAA CGATTGTGCG 2760
2761 TAAGCCAACC GAAGAACAAA AACGGATGCT    GTTACTGCCT GCCGAGGCGG TGAACGTTTC 2820
2821 ACGCAAAGGC GCGTTTACGC TTAAAGTTGG    CGGCTCCCTT AAAGGCGCGA AAACGTTTA 2880
2881 TTACAACATG GCATTAATGA ATGCCGGCGT    GAAAAAAGTT GTGGTCAGGT TTGATCCGCA 2940
2941 GCAGCTACAC AGCACGGTTT ATTGCTACAC    CCTGGACGGT CGGTTTATCT GTGAAGCGGA 3000
3001 ATGTCTGGCA CCTGTTGCAT TTAATGATGC    TGCGGCAGGC CGTGAATATC GCCGCCGCCA 3060
3061 GAAACAACTG AAATCTGCGA CGAAAGCAGC    CATTAAGGCG CAGAAACAAA TGGACGCGCT 3120
3121 GGAAGTTGCT GAACTGCTGC CGCAGATAGC    CGAACCAGCA GCACCAGAAT CACGAATTGT 3180
3181 TGGTATTTTC CGGCCTTCCG GTAATACGGA    ACGGGTGAAG AATCAGGAGC GTGATGATGA 3240
3241 ATACGAAACT GAGCGTGATG AATATCTGAA    TCATTCGCTG GATATTCTGG AACAGAACAG 3300
3301 ACGTAAAAAA GCCATTTAAT TAACGTTTAA    ACAAAATTTA ATTACGAGGT TATTCAGATG 3360
3361 AATATTTCCG ATATTCGCGC AGGACTGCGC    ACGCTTGTAG AAAATGAAGA AACCACCTTT 3420
3421 AAACAAATTG CTCTTGAGAG CGGGCTTTCT    ACCGGAACTA TCAGTAGTTT TATCAATGAT 3480
3481 AAGTACAACG GGATAACGA GCGTGTTTCA     CAAATGCTGC AACGCTGGCT GGAAAAATAT 3540
3541 CATGCAGTGG CAGAACTACC TGAACCGCCC    CGCTTTGTGG AAACGCAGAC GGTAAAACAA 3600
3601 ATCTGGACAA GTATGCGTTT TGCCAGCCTG    ACTGAAAGTA TTGCTGTTGT ATGTGGCAAT 3660
3661 CCTGGTGTGG GCAAAACCGA AGCGGCCCGT    GAATATCGCC GCACCAATAA CAATGTCTGG 3720
3721 ATGATCACCA TTACGCCATC CTGTGCCAGC    GTTCTGGAAT GTCTTACTGA ACTGGCGTTT 3780
```

Figure 14 B

```
3781 GAGCTGGGAA TGAATGACGC ACCACGCCGT AAAGGGCCGC TCTCCCGCGC CCTGCGACGT 3840
3841 CGCCTTGAAG GTACACAGGG GCTGGTTATC ATCGACGAAG CTGATCATCT TGGTGCCGAA 3900
3901 GTTCTGGAAG AACTCCGCCT GTTACAGGAA TCAACCCGTA TTGGCCTTGT GCTGATGGGA 3960
3961 AATCACCGGG TTTATTCAAA TATGACGGGG GGTAACAGAA CGGTTGAATT TGCCCGTCTG 4020
4021 TTTTCCCGTA TTGCAAAGCG CACTGCAATT AATAAAACCA AAAAAGCCGA TGTAAAAGCT 4080
4081 ATTGCGGATG CCTGGCAGAT TAACGGCGAA AAAGAACTGG AGTTATTACA GCAGATTGCG 4140
4141 CAGAAACCAG GTGCGCTTCG CATTCTGAAT CATTCACTTC GCCTTGCAGC CATGACGGCT 4200
4201 CACGGTAAAG GTGAGCGTGT TAACGAAGAT TATCTGCGTC AGGCTTTCCG TGAATTAGAC 4260
4261 CTGGACGTTG ATATTTCAAC GCTGCTGCGT AATTAAGAGG GAGAAGAAAT TATGATGGCC 4320
4321 CCGAAATATA AAAATGGCAA CGGATGCGCA GAACTGGTTA CAGGCGCGGC TGACTCTTAT 4380
4381 ACACAAGTAG CGTCCTGAAC GGAACCTTTC CCGTTTTCCA GGATCTGACT TCCATGTGAC 4440
4441 CTCCTAACAT GGTAACGTTC ATGATAACTT CTGCTCTTCA TCGTGCGCGC GACTGGGCTA 4500
4501 AATCTGTGTT CTCTTGCCGG GCGCTGGGTG ATCCTCGCCG TACTGCCCGC TTGGTTAACG 4560
4561 TCGCCGCCCA ATTGGCAAAA TATTCTGGTA AATCAATAAC CATCTCATCA GAGGGTAGTG 4620
4621 AAGCCATGCA GGAAGGCGCT TACCGATTTT ACCGCAATCC CAACGTTTCT GCCGAGGCGA 4680
4681 TCAGAAAGGC TGGCGCCATG CAAACAGTCA AGTTGGCTCA GGAGTTTCCC GAACTGCTGG 4740
4741 CCATTGAGGA CACCACCTCT TTGAGTTATC GCCACCAGGT CGCCGAAGAG CTTGGCAAGC 4800
4801 TGGGCTCTAT TCAGGATAAA TCCCGCGGAT GGTGGGTTCA CTCGGTTCTC TTGCTCGAGG 4860
4861 CCACCACATT CCGCACCGTA GGATTACTGC ATCAGGAGTG GTGGATGCGC CCGGATGACC 4920
4921 CTGCCGATGC GGATGAAAAG AAGAGTGGCA AATGGCTGGC AGCGGCCGCA ACTAGCCGGT 4980
4981 TACGCATGGG CAGCATGATG AGCAACGTGA TTGCGGTCTG TGACCGCGAA GCCGATATTC 5040
5041 ATGCTTATCT GCAGGACAGG CTGGCGCATA CCGAGCGCTT CGTGGTGCGC TCCAAGCACC 5100
5101 CACGCAAGGA CGTAGAGTCT GGGTTGTATC TGATCGACCA TCTGAAGAAC CAACCGGAGT 5160
5161 TGGTTGGCTA TCAGATCAGC ATTCCGCAAA AGGGCGTGGT GGATAAACGC GGTAAACGTA 5220
5221 AAAATCGACC AGCCCGCAAG GCGAGCTTGA GCCTGCGCAG TGGGCGCATC ACGCTAAAAC 5280
5281 AGGGGAATAT CACGCTCAAC GCGGTGCTGG CCGAGGAGAT TAACCCGCCC AAGGGTGAGA 5340
5341 CCCCGTTGAA ATGGTTGTTG CTGACGCGCG AACCGGTCGA GTCGCTAGCC CAAGCCTTGC 5400
5401 GCGTCATCGA CATTTATACC CATCGCTGGC GGATCGAGGA GTTCCATAAG GCATGGAAAA 5460
5461 CCGGAGCAGG AGCCGAGAGG CAACGCATGG AGGAGCCGGA TAATCTGGAG CGGATGGTCT 5520
5521 CGATCCTCTC GTTTGTTGCG GTCAGGCTGT TACAGCTCAG AGAAAGCTTC ACGCTGCCGC 5580
5581 AAGCACTCAG GGCGCAAGGG CTGCTAAAGG AAGCGGAACA CGTAGAAAGC CAGTCCGCAG 5640
5641 AAACGGTGCT GACCCCGGAT GAATGTCAGC TACTGGGCTA TCTGGACAAG GAAAACGCA 5700
5701 AGCGCAAAGA GAAAGCAGGT AGCTTGCAGT GGGCTTACAT GGCGATAGCT AGACTGGGCG 5760
5761 GTTTTATGGA CAGCAAGCGA ACCGGAATTG CCAGCTGGGG CGCCCTCTGG TAAGGTTGGG 5820
5821 AAGCCCTGCA AAGTAAACTG GATGGCTTTC TTGCCGCCAA GGATCTGATG GCGCAGGGGA 5880
5881 TCAAGATCTG ATCAAGAGAC AGGATGAGGA TCGTTTCGCA TGATTGAACA AGATGGATTG 5940
5941 CACGCAGGTT CTCCGGCCGC TTGGGTGGAG AGGCTATTCG GCTATGACTG GGCACAACAG 6000
6001 ACAATCGGCT GCTCTGATGC CGCCGTGTTC CGGCTGTCAG CGCAGGGGCG CCCGGTTCTT 6060
6061 TTTGTCAAGA CCGACCTGTC CGGTGCCCTG AATGAACTGC AGGACGAGGC AGCGCGGCTA 6120
6121 TCGTGGCTGG CCACGACGGG CGTTCCTTGC GCAGCTGTGC TCGACGTTGT CACTGAAGCG 6180
6181 GGAAGGGACT GGCTGCTATT GGGCGAAGTG CCGGGGCAGG ATCTCCTGTC ATCTCACCTT 6240
6241 GCTCCTGCCG AGAAAGTATC CATCATGGCT GATGCAATGC GGCGGCTGCA TACGCTTGAT 6300
6301 CCGGCTACCT GCCCATTCGA CCACCAAGCG AAACATCGCA TCGAGCGAGC ACGTACTCGG 6360
6361 ATGGAAGCCG GTCTTGTCGA TCAGGATGAT CTGGACGAAG AGCATCAGGG GCTCGCGCCA 6420
6421 GCCGAACTGT TCGCCAGGCT CAAGGCGCGC ATGCCCGACG GCGAGGATCT CGTCGTGACC 6480
6481 CATGGCGATG CCTGCTTGCC GAATATCATG GTGGAAAATG GCCGCTTTTC TGGATTCATC 6540
6541 GACTGTGGCC GGCTGGGTCT GGCGGACCGC TATCAGGACA TAGCGTTGGC TACCCGTGAT 6600
6601 ATTGCTGAAG AGCTTGGCGG CGAATGGGCT GACCGCTTCC TCGTGCTTTA CGGTATCGCC 6660
6661 GCTCCCGATT CGCAGCGCAT CGCCTTCTAT CGCCTTCTTG ACGAGTTCTT CTGAGCGGGA 6720
6721 CTCTGGGGTT CGAAATGACC GACCAAGCGA CGCCCAACCT GCCATCACGA GATTTCGATT 6780
6781 CCACCGCCGC CTTCTATGAA AGGTTGGGCT TCGGAATCGT TTTCCGGGAC GCCGGCTGGA 6840
6841 TGATCCTCCA GCGCGGGGAT CTCATGCTGG AGTTCTTCGC CCACCCCGGA ATTGGTACCC 6900
6901 ATATGGAATT CGGATCCGTC GACATCGATG CGGCCGCCGA TCGCGACAAT TCCGTTTTCG 6960
6961 CATTTATCGT GAAACGCTTT CGCGTTTTTC GTGCGCCGCT TCA                 7003
         |    10    |    20    |    30    |    40    |    50    |    60
```

PROTEIN FUSION METHOD AND CONSTRUCTS

BACKGROUND OF THE INVENTION

Rational protein design. The main goal of modern protein chemistry is to be able to design proteins with desired functions. The approach taken by the majority of scientists has been called rational protein design, which is highly dependent on knowledge of protein structure in three dimensions and protein folding. While an extremely powerful tool, rational protein design is currently limited to a small subset of enzymes: those with well defined three dimensional structures. The classic examples include proteins such as subtilisin from several Bacillus sp. (Wells, Powers et al. Proc Natl Acad Sci USA. (1987). 84: 1219–1223.) and T4 lysozyme (Matsumura, Becktel et al. (1989). Proc Natl Acad Sci USA. 86: 6562–6566.). The three dimensional organization of the amino acid side chains of the protein must be known at high resolution, and often protein/substrate and mutant structures must be known as well. While this method is useful, it is expensive, time consuming and requires difficult predictions. Even with a complete three dimensional X-ray crystallography structure in hand, it has proven difficult to design proteins with specific desired activities. To address these problems, methods which allow the accelerated evolution of proteins in vivo or in vitro can take advantage of natural mutagenic mechanisms and their resulting variability.

Protein fusions. Protein (translational) fusion can be created by the joining of translational sequences from two different genes to create a hybrid protein molecule. These applications have traditionally included the study of gene expression in microorganisms and eukaryotes (Casadaban, Martinez-Arias et al. (1983). Recombinant DNA. Methods in Enzymology. 100: 293–308.).

The use of protein fusion in vitro to generate hybrid (chimeric) proteins has gained importance in the development of novel or multifunctional enzyme activities. Applications include using protein domains to aid in protein purification (Sherwood. (1991). TIBTECH. 9: 1–3.) or to tag proteins for delivery to specific cellular locations (Crozel, Lazdunski et al. (1984). FEBS Lett. 172: 183–188; Moore and Kelly. (1986). Nature. 321: 443–446; Roitsch and Lehle. (1991). Eur J Biochem. 195: 145–50.). Domain shuffling between different proteins shows promise to create protein products with unique uses, often to bind a particular enzymatic activity to a site of interest (Panayotatos, Fontaine et al. (1988). Molecular genetics of bacteria and phages: prokaryotic gene regulation. 174.), as a reporter system for protein-protein interactions (Fields and Song. (1989). Nature. 340: 245–246.), to study the relatedness of different proteins (Caramori, Albertini et al. (1991). Gene. 98: 37–44.) or as targeted pharmaceuticals (Pastan and FitzGerald. (1991). Science. 254: 1173–1177.). Finally, another promising application of protein fusion to biotechnology is in creating multi-catalytic enzymes which are important in biocatalysis since they represent an alternative to co-immobilization and chemical crosslinking to create multienzyme systems (Bulow and Mosbach. (1991). TIBTECH. 9: 226–231.).

Problems in the development of protein fusions. Unfortunately, the construction of functional hybrid proteins can require an extensive knowledge of a protein's structure and functional domains in order to select a proper site for fusion. Many attempts have failed to produce the desired properties (Bowie and Sauer. (1989). J Bio Chem. 264: 7596–7602; Ellis, Morgan et al. (1986). Proc Natl Acad Sci, USA. 83: 8137–8141; Guan and Rose. (1984). Cell. 37: 779–787; Hellebust, Murby et al. (1989). BioTech. 7: 165–168.). Random deletions can be made to fuse two domains, but this is typically done for only one domain at a time, and the cost and time involved in such trial and error efforts can be substantial. In addition, while some gene fusions can be used to stabilize proteins, unstable structures are often formed which are recognized by the cellular degrading machinery (Bowie and Sauer. (1989). J Bio Chem. 264: 7596–7602; Hellebust, Murby et al. (1989). BioTech. 7: 165–168.). Also, even with the advanced level of molecular biological techniques available today, cloning remains a labor-intensive procedure, the results of which are not trivially predictable.

Several tools have been developed to make the construction of protein fusions simpler. These tools include new plasmid systems with convenient restriction sites (Shapira, Chou et al. (1983). Gene. 25: 71–82.), and a method for making gene fusions using the Polymerase Chain Reaction (PCR) so that convenient restriction sites are not required (Horton, Hunt et al. (1989). Gene. 77: 61–8.). None of these approaches, however, offers a truly simple way of making random protein fusions which eliminates the labor-intensive, trial and error aspects of traditional techniques, especially in the case when at least one of the two domains being studied has not yet been well characterized.

Transposons. Transposable elements are mobile stretches of DNA which are defined by two end terminals, usually denoted attL and attR at the left and right attachment ends respectively. Natural transposable elements contain DNA coding for transposases, and often portable genes conferring traits such as resistance to antibiotics. Some transposable elements can insert randomly into targeted DNA while others are sequence specific in their insertion sites. Transposons have been implicated as having a major role in evolution, and there is evidence for natural multifunctional enzymes having originated from the natural fusion of different protein domains.

Scientists have taken advantage of transposons to transport reporter genes for use in studying gene expression. These include transcriptional (Type I) fusions and translational (Type II) fusions. Transcriptional fusions, unlike translational fusions, place a reporter gene under the control of another promoter, but do not translationally fuse two protein domains. Translational fusions have generally been made to link a reporter gene carried inside the transposon to the translational frame of the target gene so that the reporter gene is expressed under direct control of the transcription and translation signals of the target gene of interest to study gene regulation. This requires that an open reading frame extend through the end of the transposable element to join an internal reporter protein to external translational sequences. This usually results in complete inactivation of the target gene.

Mu and the Transposing Bacteriophage. Bacteriophage Mu represents a class of transposons known as transposable bacteriophage which both function as a virus and a transposon. Mu replicates itself by transposing at high frequency, but can also integrate randomly into its host's genome as a lysogen. Mu is a model system for other transposable bacteriophage which are generally highly homologous. These include the Pseudomonas phage D3112, D108, and several other phage.

Because of the randomness of Mu insertions, and the high levels of transposition which can be generated by Mu strains containing a temperature sensitive transposition repressor (Mucts strains), Mu has been developed into a genetic tool to study gene expression in bacterial systems. Transposition of Mu derivatives has allowed scientists to perturb and examine the basic components critical to protein expression and translation. The most commonly used Mu derivatives include reporter genes which have been integrated into the Mu genome.

Type I Fusions. Type I transcriptional fusions have been used to study gene expression and regulation by co-opting the native transcriptional signal to express the exogenous reporter gene. For example for gene expression in E. coli, yeast, and Drosophila development.

Type II Fusions. Type II fusions have also been used to study gene expression and regulation, but in this case not only co-opt the transcriptional signals, but any translational signals as well to express the reporter gene. In this type of system the protein product usually only expresses the activity of the reporter exogenous gene.

MudII elements are mini-Mu deletion elements which are type II Mu transposable elements. Examples of these include β-galactosidase fusion elements, where a β-galactosidase (lacZ) reporter gene is inserted via transposable elements to detect transcription and translation of regulated gene systems. This usually results in the inactivation of the targeted gene.

Two types of Mu protein fusions have been developed, lacZ fusion elements and nptI fusion elements (Symonds, Toussaint et al. (1987). *Phage Mu*) The lacZ elements have been used to study translation regulation, determination of the translation phase of target genes, infer the location of a protein fusion by hybrid protein size, determine amino terminal sequence, and raise antibodies to regions of the protein of interest. By far the major goal of these studies has been to determine mechanisms of gene expression in the studied organisms.

The nptI system was designed to perform transposon-tagging since nptI is known to function as an aminoglycoside resistance gene in a variety of organisms. Transposon tagging is a method of creating an mutant by inserting a transposon with a selectable marker into the gene of interest so that mutants which inactivate the gene can be identified and maintained. This element is useful since it allows the nptI to be directly linked to the transcription/translation system of the organism being studied.

In these studies there has been no emphasis on creating novel proteins with new activities using these transposable elements. More importantly, these Mu elements are restricted to making amino-terminal fusions to the reporter protein. In these cases the inserted reporter gene is fused to the carboxy-end of the truncated targeted protein, terminating inside the Mu. If the transposable element were to insert before the amino terminal of a targeted gene, functional translation could only occur on the marker gene by itself, and no translation of the target gene would occur.

Problems with Mu. Unfortunately, available Mu elements had several problems. First, it has not been demonstrated that Mu elements can be readily used as a general method for the development of fusion proteins with two active domains. Second, the Mu elements used thus far for creation of protein fusions can not be used for construction of "carboxy-terminal" fusions since they did not have an open reading frame extending into the element. Third, the Mu elements previously used have long linker regions which incorporate a 40 amino acid linker between the fused domains. This could create protein folding problems or unwanted domain interactions. Fourth the currently existing Mu elements had only a single restriction site for the insertion of protein domains. Finally, although Mu elements which had deleted ends existed, it was not known whether they would transpose well with additional sequences added in such close proximity to the right end and whether the intervening linker region which would join the two protein domains would interfere with the construction of active chimeric proteins.

Other transposons. Other transposons have been used in a similar manner as Mu to create lac fusions to study gene expression. These include Tn10 and Tn917 (Berg and Howe. (1989). *Mobile DNA*).

The Tn5 element has also been used to construct phoA fusions in vivo. Fusions with alkaline phosphatase (phoA) have also been used to probe the structure of membrane bound proteins (Lloyd and Kadner. (1990). J Bacteriol. 172: 1688–93.). In general, these transposons have been used to study the membrane topology structure of a particular gene and protein secretion. The resultant fusion proteins are also limited to amino-terminal fusion of the reporter PhoA reporter protein resulting in fusion at the carboxy end of the targeted gene.

In general, these types of fusions have been applied to the study of gene expression. These elements were constructed with truncated marker proteins that extend through the end of the transposon. Transposition of the element can create an in-frame fusion with a target gene, thereby activating expression. Mini-Mu elements are used because they transpose at high frequencies, insert randomly, and can be packaged along with a target plasmid and transduced to a new cell (Symonds, Toussaint et al. (1987). *Phage Mu*). Some of the more pertinent work that has been done in the area of transposable elements are detailed in the following.

Namgoong et al., (1994), teach that the Mu transposition reaction attachment sites attL and attR can promote the assembly of higher order complexes held together by non-covalent protein-DNA and protein-protein interactions. (Namgoong, Jayaram et al. (1994). J Mol Biol. 238: 514–527.)

Harel et al., (1990), teach that in Mu helper-mediated transposition packaging the left end contains an essential domain defined by nucleotides 1 to 54 of the left end (attL). At the right end (attR), they teach that the essential sequences for transposition require not more than the first 62 base pairs (bp), although the presence of sequences between 63 and 117 bp from the right end increase transposition frequency about 15-fold. (Harel, Dupliessis et al. (1990). Arch Microbiol. 154: 67–72.)

Groenen and van de Putte (1986), teach that the Mu A protein binds weakly to sequences between nucleotides 1 to 30 on the right end (R1) and between nucleotides 110 and 135 on the left end (L2). Mutations in these weak A binding sites have a greater effect on transposition than mutations of corresponding base pairs in the stronger A binding sites, located adjacent to these weak A binding sites. (Groenen and van de Putte. (1986). J Mol Biol. 189: 597–602.)

Groenen and et al. (1985) teach the DNA sequences at the end of the genome of bacteriophage Mu that are essential for transposition. (Groenen, Timmers et al. (1985). Proc Natl Acad Sci, USA. 82: 2087–2091.)

Lloyd and Kadner teach the how to probe the topology of the uhpT sugar phosphate transporter using a Tn5phoA element. (Lloyd and Kadner. (1990). J Bacteriol. 172: 1688–93.)

*Phage Mu* (1987), Cold Spring Harbor Laboratory Press (Symonds, et al eds.) teaches general methods for handling and working with bacteriophage Mu as a transposon, and describes the various uses of mini-Mu elements including the construction of Mu transcriptional and translational fusions.

Silhavy and Beckwith (1985) teaches the various uses of lac fusions for the study of biological problems. (Silhavy and Beckwith. (1985). Microbiol Rev. 49: 398–418.)

*Mobile DNA*, (1989), American Society for Microbiology, Publishers. (Berg, Howe, eds) describes transposons.

Casadaban, et al. (1983) Methods in Enzymol, provides a good general review of β-galactosidase gene fusions for the study of gene expression. (Casadaban, Martinez-Arias et al. (1983). Recombinant DNA. Methods in Enzymology. 100: 293–308.)

BRIEF DESCRIPTION OF DRAWINGS

FIG. 2. Mini-Mu elements with Deleted ends SEQ ID NOS. 3–13.

FIG. 3. Example reading frames and restriction sites of the new polylinker Mu elements SEQ ID NOS. 15–20.

FIG. 12. Scheme for generating amino- or carboxy-terminal fusion proteins.

FIG. 13. PCR sequences for construction of new target plasmid SEQ ID NOS. 22 and 23.

FIG. 14. Sequence of a transposable element. The sequence of transposable element MueII315 is given (originally constructed on plasmid pIVP315) SEQ. ID. NO. 24.

SUMMARY OF THE INVENTION

Figure 1:
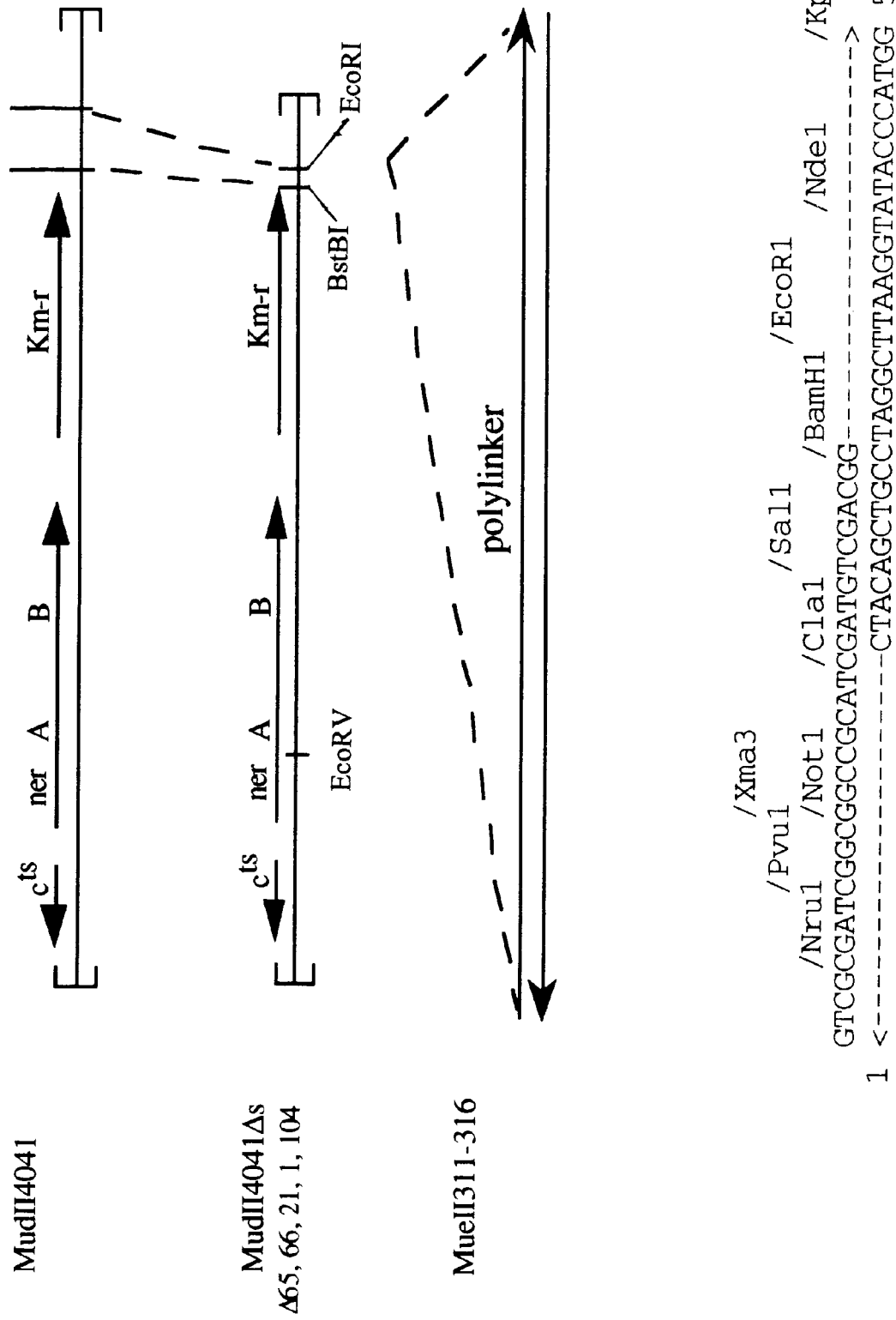
FIG. 1. Maps of polylinker mini-Mu elements constructed SEQ ID NOS. 1 and 2.

The instant invention encompasses transposable elements for generating functional fusion proteins comprising at least a left attachment site and a right attachment site where there is an open reading frame in both directions through at least one of the ends. In one embodiment the instant invention encompasses a transposable element containing a polylinker that is located adjacent to one end of the transposable element, while still allowing for open translational reading frames to enter and exit the near end. In another embodiment, the invention encompasses a transposable element as in containing a polylinker with an inserted exogenous DNA sequence. This exogenous DNA can encode for a complete protein, a functional portion of a protein, an expressible or inducible segment of DNA, or any other suitable DNA sequence. Also encompassed by the instant invention is a transposable element, where the expression of the exogenous DNA is under controlled regulation of a promoter, enhancer, or repressor which target sequences can be a part of the exogenous DNA segment, or a part of the transposable element construct. In a preferred embodiment, the instant invention encompasses a transposable element of containing a right attachment site of 50 to 62 nucleotides. The instant invention encompasses a transposable element for generating functional fusion proteins comprising at least a left attachment site and a right attachment site where there is an open translational reading frame extending out through one of the ends of the element. The instant invention also encompasses, in one embodiment, full-length attachment sites, in which translational open reading frame interrupting stop codons, which prevent the reading frame from extending out of the transposable element through a attachment site that is within 400 bases, have been removed by selective substitution of nucleotides in the nucleic acid sequence. Thus the instant invention also encompasses a transposable element for generating functional fusion proteins comprising at least a left attachment site and a right attachment site where the endogenous stop codons that would prevent translation through the ends have been removed by point mutation. In particular, the instant invention provides for a transposable element which contains the DNA sequence of FIG. 14 SEQ ID NO. 24.

In another particular embodiment of constructs of the instant invention is a transposable element containing the Protein A domain which allows functional protein fusion with a target protein. The instant invention also embodies a transposable element which allows for functional carboxy or amino terminal fusion of the Protein A domain to a targeted protein sequence. Thus the instant invention provides for methods of making Protein A fusion proteins which are either amino- or carboxy-terminal fusion proteins.

The methods and constructs of the instant invention also provide for a cell wherein a transposable element for generating functional fusion proteins, comprising at least a left attachment site and a right attachment site with a protein domain whose translational open reading frame extends through one of the ends of the element, is integrated into the cell genome. In one embodiment, the transposable element is integrated into an autonomously replicating DNA form within a cell of the instant invention.

The instant invention encompasses a method for generating functional fusion proteins, with a transposable element which contains at least a left attachment site and a right attachment site where there is an open reading frame in both directions through at least one of the ends, comprising insertion of an exogenous DNA sequence into the transposable element, transposing into a target DNA sequence with the transposable element, detecting the presence of the exogenous DNA insert, and selecting for the presence of the exogenous DNA insert. Another embodiment of the instant invention encompasses a method for in vitro or in vivo protein fusion in a target organism genome comprising constructing a transposable element with a left attachment site, a polylinker, and a right attachment site of between 50 and 62 nucleic acid base pairs, inserting within the polylinker an exogenous DNA sequence, transposing the transposable element into a target organism genome, expanding the target organism, isolating protein, and screening for fusion protein containing the translated exogenous DNA. In particular the instant invention encompasses a right attachment site of 58 nucleotides in length.

Another particular embodiment of the instant invention encompasses a method for in vitro or in vivo carboxy terminal translational protein fusion in a target organism genome comprising constructing a transposable element with a left attachment site and a right attachment site of between 50 and 62 nucleic acid base pairs, inserting within the transposable element an exogenous DNA sequence, transposing the transposable element into a target organism genome, expanding the target organism, isolating protein, and screening for fusion protein containing the translated exogenous DNA. In a particular embodiment the right attachment site is 58 nucleotides in length. The instant invention also provides for a method for in vitro or in vivo amino terminal translational protein fusion in a target organism genome comprising constructing a transposable element with a left attachment site attL and a right attachment site attR of between 50 and 62 nucleic acid base pairs, inserting within the transposable element an exogenous DNA sequence, transposing the transposable element into a target organism genome, expanding the target organism, isolating protein, and screening for fusion protein containing the translated exogenous DNA. In a preferred embodiment of the instant invention, the attachment sites are derived from the Mu family of transposable elements. In another preferred embodiment of the instant invention, the right attachment site is 58 nucleotides in length.

The instant invention also encompasses a plasmid for inserting target sequences for protein fusion which comprises in the following order, a transcription termination site, an extended translational target region with no stop codons, and a polylinker sequence for cloning protein domains into containing no stop codons in frame with the translational target region. In another embodiment, the plasmid additionally contains a screenable marker fused to the translational target region, and the polylinker reading frame located after the polylinker region.

Thus the instant invention teaches the use of transposable elements with deletions in an end terminal attachment site which result in multiple reading frames in both directions through the end, and allows for the generation of functional protein fusions. In one particular embodiment the particular end is the right end attachment site of Mu known as attR. The invention specifically teaches constructs which allow for carboxy-terminal and/or amino-terminal fusion events to occur. In one embodiment, the instant invention encompasses a transposable element comprising a left attachment site attL, and a right attachment site of no more than 58 nucleic acid base pairs which will transpose an exogenous DNA sequence into a target DNA sequence. In a preferred embodiment, the attachment sites are derived from the Mu family of transposable elements. The teachings of the instant invention can also be applied to create similar constructs which allow for similar translation reading frames via the left attachment site. The instant invention also encompasses transposable elements comprising a left attachment site attL, a polylinker, and a right attachment site. In this embodiment, the polylinker allows for multiple restriction sites which allow for the convenient insertion of exogenous DNA segments. In a preferred embodiment, the transposable element is constructed such that it allows for open reading frames in both orientations. In a further embodiment, the exogenous DNA inserted within the transposable element is under controlled expression by a promoter, enhancer or repressor element. In a preferred embodiment, the instant invention encompasses a transposable element comprising a left attachment site attL, a polylinker region, and a right attachment site of no more than 58 nucleic acid base pairs derived from the Mu family of transposable elements, which will transpose an exogenous DNA sequence into a target DNA sequence and allow for open reading frames in both orientations.

The instant invention provides for the use of a transposable element comprising a left attachment site attL, an exogenous DNA, and a right attachment site for generating in vivo protein fusions in a target DNA. The target DNA can be plasmid DNA, DNA segments, genomic DNA, or other DNA targets. In a preferred embodiment of the instant invention, the right end of the transposable element consists of no more than 58 nucleic acid base pairs derived from the Mu family of transposable elements. The instant invention encompasses methods for using transposable element constructs with deletions in the right end for generating fusion proteins in vitro and in vivo. A method of the instant invention allows for the rapid and efficient generation of alternatively fused proteins suitable for screening for activity. In one embodiment of the method of the instant invention generates fusion proteins in which the exogenous DNA segment has been transposed such that the resultant fusion protein functionally expresses the exogenous protein as a amino-terminal fusion to the carboxy end of a targeted protein. In a further embodiment of a method of the instant invention, the transposable element causes the insertion of the exogenous DNA such that the functionally expressed fusion protein consists of the exogenous protein at the amino end, linked to the endogenous protein at the carboxy end of the fusion protein.

The instant invention provides for a method for in vivo protein fusion in a target organism genome comprising constructing a transposable element with a left attachment site attL, a polylinker, and a right attachment site of no more than 58 nucleic acid base pairs, inserting within the polylinker an exogenous DNA sequence, transposing the transposable element into a target organism genome, expanding the target organism, isolating protein, and screening for fusion protein containing the translated exogenous DNA. In a preferred embodiment, the instant invention provides for the in vivo carboxy terminal translational protein fusion in a target organism genome comprising constructing a transposable element with a left attachment site attL and a right attachment site attR of no more than 58 nucleic acid base pairs, inserting within the transposable element an exogenous DNA sequence, transposing the transposable element into a target organism genome, expanding the target organism, isolating protein, and screening for fusion protein containing the translated exogenous DNA. In another preferred embodiment, the instant invention provides for in vivo amino terminal translational protein fusion in a target organism genome comprising constructing a transposable element with a left attachment site attL and a right attachment site attR of no more than 58 nucleic acid base pairs, inserting within the transposable element an exogenous DNA sequence, transposing the transposable element into a target organism genome, expanding the target organism, isolating protein, and screening for fusion protein containing the translated exogenous DNA.

In a further embodiment of the instant invention, the method for generating novel fusion proteins encompasses the use of transposable elements in which the stop codons present in the attR region have been removed by point mutation such that there is an open reading frame leading out of the transposable element, allowing for the amino-terminal or carboxy-terminal fusion of the exogenous protein with the targeted protein by a linker which is translated from the attR region.

The constructs and methods of the instant invention are useful for the rapid and efficient generation of functional fusion proteins. The constructs and methods of the instant invention are useful in that they reduce the labor intensive burdens that accompany generation of protein fusions by traditional molecular cloning techniques.

The following descriptions and examples are meant only by way of illustration of the instant invention, and are in no way intended to limit the scope of the instant invention. One with ordinary skill in the art will be able to understand and use the descriptions of the instant specification to use all of the embodiments which are contemplated and encompassed by the contructs and methods of the instant invention.

DESCRIPTION OF THE INVENTION

The instant invention provides constructs and methods for the rapid and efficient generation of functional fusion protein products with either carboxy-terminal or amino-terminal fusions. Functional fusion proteins are those which retain some of the activity of the original domains, and/or those which have a newly created activity. Throughout this specification, reference is made to two types of fusions: carboxy terminal fusions and amino terminal fusions. In this text we use amino and carboxy terminal fusions to refer to the end of the domain inside of the Mu elements which is fused to the target molecule. Thus, carboxy terminal fusion elements are those with a protein domain inside of the Mu which extends out of the Mu element such that the exogenous protein is fused to the amino end of the endogenous protein. The amino terminal fusion elements are those that create fusions with a target gene extending into the element such that the exogenous protein is fused to the carboxy terminal of the endogenous protein.

FIG. 12 shows an overview for generating both amino- and carboxy- terminal fusion proteins with the transposable elements is outlined. A domain of interest is inserted in one of two possible orientations into the end of a transposable element, such that a continuing open reading frame extends out through the element (for carboxy-terminal fusions) or in through the element (for amino-terminal fusions). Transposition into a target sequence allows random generation of hybrid proteins. Functional fusions can be selected or screened for.

The instant invention provides for mini-Mu transposon elements with convenient polylinker sites for inserting protein domains into the transposable element. The instant invention also provides for macro-Mu elements. The transposable elements of the instant invention have been designed to have a shorter transposon end which becomes incorporated into the fusion product while still retaining their high transposition frequencies. Unlike other elements used to date they can be used to make both amino and carboxy-terminal fusions since they have open reading frames extending in both directions. The examples below demonstrate the application of the teachings of the instant invention for using the new elements to create protein fusions with two fully active domains and their usefulness as a general tool for protein fusion. Other examples demonstrate new features such as regulatable promoters incorporated into the transposable element, which can allow control of expression for promoterless domains or domains which may exhibit some degree of lethality to the cell. The constructs and methods described here allow high frequency random fusion of two domains at multiple sites so that the optimal fusion junctions can be selected.

The constructs and teachings of the instant invention provide a powerful tool which will aid in the development of new enzymes for biocatalytic applications such as bioremediation and industrial biocatalysis, and for other industrial applications such as biosensors and strain development. Many different combinations of fusions between two domains can be generated rapidly and screened for activity. As an extension of protein evolution, this will be a powerful technique for production of novel chimeric proteins.

In contrast to the difficulties inherent in a traditional rational protein design approach which employs traditional molecular biological techniques to generate fusion proteins, the instant invention provides for rapid and efficient "randomized experimentation" whereby the transposon fusion events are utilized to generate a panel of fusion proteins. From this panel of fusion proteins, selection for functionally expressed products, results in efficient screening for successful fusions.

While traditional experimentation with transposable elements resulted in the ablation of endogenous protein translation, and substitution of the translation and expression of the reporter gene for study of gene expression and regulation, the instant invention teaches modifications of these elements which allow for the generation of functional fusion proteins which can contain novel activities. The instant invention teaches for the first time the construction of transposable elements which can transpose exogenous DNA into target DNA in both orientations which can result in the functional expression of fusion proteins which have the exogenous protein linked either on the amino-end, or at the carboxy-end of the target protein.

The constructs and methods of the instant invention are not limited to the use of proteins with known crystal structures, but is capable of generating functional fusion proteins from the randomized combination of functional domains. Instead of being limited to the mere tethering of functional domains, the constructs and methods of the instant invention allow for the fusion protein product to occur at randomized "truncated" sites of the target protein. This allows for the rapid generation of and screening for functional fusion proteins that are incorporated into a truncated form of the targeted protein.

Thus the instant invention has provided for creating new mini-Mu elements with polylinkers for domain insertion and open reading frames both into and out of the element. The elements have reduced ends while maintaining their high transposition frequency.

The constructs of the instant invention and examples below show the ability of these elements to make carboxy-terminal protein fusions between a Protein A domain carried on the element and both selectable (chloramphenicol-acetyl transferase) and screenable (β-galactosidase) proteins.

The constructs of the instant invention are useful for making amino-terminal fusions and demonstration of kinetic observations with β-galactosidase showing that the Km value is maintained even if it is fused to different locations.

While the constructs and methods of the instant invention are functional in an in vitro setting, a major advantage of the instant invention is the application of in vivo settings for generating functional fusion proteins. The development of an in vivo protein engineering system that is both versatile and easy to use will have a significant impact on the way proteins with specific activities are defined. This invention results in the development of a refined system for the in vivo engineering of proteins. The constructs and methods of the instant invention are powerful enhancements to the genetic tools available to the molecular biologist. The constructs of the instant invention can be provided as kits for the engineering of proteins.

One might imagine that an in vivo system may have problems since biological systems are limited to the properties of the particular system. One of the advantages of the Mu transposition system is that it is the most general and well defined of the transposition systems available (Symonds, Toussaint et al. (1987). *Phage Mu.*). The biological properties of the system are advantages which make Mu simple to use. Mu provides very convenient methods for isolating independent insertion events by transducing them to a new cell. Creation of insertions requires only a temperature shift. We have favored the Mu transposition system from the start because an untrained technician may be taught to reproducibly use the Mu system in just a few days. While the initial design and construction of a Mu system can be difficult, the finished system's simplicity lends itself to commercialization. There is much to be said for in vitro systems. The in vivo system of the instant invention was intended to be an additional protein engineering tool to enhance the methods of producing novel active protein fusions when used in conjunction with basic in vitro methods, or with additional novel in vitro methods of the instant invention.

There has been no previous demonstration of the altered transcription through the end of a Mu element. Specifically, transcription through the end of the Mu element might reduce transposition frequencies. Surprisingly we have found that the transcription of the Protein A gene through the end of Mu did not alter transposition frequencies.

The instant invention encompasses both the amino and carboxy-terminal fusion elements because they are useful in different applications. The carboxy-terminal element is more useful for making fusions with a cDNA which has been cloned from a eukaryotic organism, especially if one wants to ultimately express it in another organism. Amino-terminal elements are more useful for some applications because they can only be activated by a fusion event if they are missing the start codon. The instant specification teaches new Mu elements with promoters for expression in the experimental design. One of the main commercial applications of the system is to generate new enzymes for medical or industrial uses both in vivo and in vitro. *E. coli* will likely be the production organism if there are no post-translational modification problems associated with the enzymes. But it is possible to use any Mu compatible strain as the production organism.

EXAMPLE 1

Strains, Media, and Propagation

Strains. The strains, plasmids, and phage used in this work are listed in Table I. General microbiological and molecular biological techniques have been described by Miller (Miller, J. H. (1972). *Experiments in Molecular Genetics*. Cold Spring Harbor, N.Y., Cold Spring Harbor Laboratory) and Sambrook et al (Sambrook, J., T. Maniatis and E. F. Fritsch. (1989). *"Molecular Cloning: A Laboratory Manual."*. Cold Spring Harbor, N.Y., Cold Spring Harbor Laboratory).

Methods for working with Mu transposons are generally outlined in (Symonds, Toussaint et al. (1987). *Phage Mu*).

TABLE 1

| Plasmid/Strain | Description | Transposon | Source |
| --- | --- | --- | --- |
| 1. Plasmids | | | |
| pKSU+ | Bluescript II cloning plasimd, rep pMBI, up copy #,lacIPOZ'A | | Stratagene |
| pACYC184 | Tc$^r$ Cm$^r$ rep p15A | | (Chang and Cohen. (1978). J Bacteriol. 134: 1141-1156.) |
| Ftet | pOX8 Δ HindIII | | M. Groyer |
| pMC1817 | lac Z vector, Ap$^r$ | | (Casadaban, Martinez-Arias et al. (1983). Recombinant DNA. Methods in Enzymology. 100: 293–308.) |
| pMC1871 | lac Z fusion vector (amino truncated), Ap$^r$ | | (Casadaban, Martinez-Arias et al. (1983). Recombinant DNA. Metbods in Enzymology. 100: 293–308.) |
| pCM7 | pBR327 with promoterless cat gene cloned into HindIII site in tet promoter. Ap$^r$ | | Pharmacia |
| pBR327 | pBR322 deletion, Ap$^r$, Tc$^r$ | | Rodgeny |
| pRIT5 | Protein A fusion vector, Ap$^r$ | | Pharmacia |
| pEZZ18 | Synthetic Protein A fusion vector, Ap$^r$ | | |
| pBC4041 | MudII4041 vector, Ap$^r$, Km$^r$. BamHI site. attR = 118bp | MudII4041 | (Castilho, Olfson et al. (1984). J Bacteriol. 158: 488–495.) |
| pNEKΔ65 | pBC4041 right end deletion. EcoRI linker, attR = 117bp remaining | MudII4041Δ5 | Casadaban |
| pNEKΔ66 | pBC4041 rigbt end deletion. EcoRI linker, attR = 83bp remaining | MudII4041Δ66 | Casadaban |
| pNEKΔ21 | pBC4041 right end deletion. EcoRI linker, attR = 71bp remaining | MudII4041Δ21 | Casadaban |
| pNEKΔ1 | pBC4041 right end deletion. EcoRI linker, attR = 58bp remaining | MudII4041Δ1 | Casadaban |
| pNEKΔ104 | pBC4041 right end deletion. EcoRI linker, attR = 18bp remaining | MudII4041Δ104 | Casadaban |
| pIVP301, 302 | pKSII + (Sma) + Protein A AseI fragment under T7 promoter (fwd, rev) | | this work |
| pIVP303, 304 | pNEKΔ66 EcoRI + promoterless Protein A from pIVP302 (fwd, rev) | MueII303, 304 | this work |
| pIVP307, 308 | pNEKΔ1 EcoRI + promoterless Protein A from pIV302 (fwd, rev) | MueII307, 308 | this work |
| pIVP311, 312 | pNEKΔ66 EcoRI filled-in + polylinker (both orientations) | MueII311, 312 | this work |
| pIVP313, 314 | pNEKΔ21 EcoRI filled-in + polylinker (both orientations) | MueII313, 314 | this work |
| pIVP315, 316 | pNEKΔ1 EcoRI filled-in + polynnker (both orientations) | MueII315, 316 | this work |
| pMW101 | pIVP315 with double Protein A insert | MueII101 | this work |
| pMW102 | pIVP315 with protein A insert (double vector) | MueII102 | this work |
| pGG101-200 | pMC1817::MudII1734 | MudII1734 | this work |
| pGG201-300 | PBR327::MudII1734, usually in tet gene | MudII1734 | this work |
| 2. *E. coli* Strains | | | |
| BAC101 | M882OTR Mucts62::MudII4041 | | MudII4041(Castilho and Casadaban. (1991). J Bacteriol. in press.:.) |
| M8820 | F- aaD139A(cirCOIBA leu)7697 Δ(proAB arg F lac IPOZY A)X111 rps L | | (Castilho, Olfson et al. (1984). J Bacteriol. 158: 488–495.) |
| M8820 Mucts | M8820 Mucts62 | | Mucts(Castilho, Olfson et al. (1984). J Bacteriol. 158:488–495.) |
| MC1040-2 | F- aaD139 araB::Mucts62 Dlac X74 gal U gal K rpsL | | Mucts Casadaban |

TABLE 1-continued

| Plasmid/Strain | Description | Transposon | Source |
|---|---|---|---|
| MG1655.10 Ftet | W1485 F- no Γδ Ftet | | Darzins |
| MG1655.10 Mucts | MG1655.10 Mucts62 | Mucts | Casadaban |
| POII1734D | pro +lac MudII1734 (Km$^r$) | MudII1734 | P. Olfson |
| TGPE1 | MG1655.10 Mucts::MueII303 | MueII303 | this work |
| TGPE3 | MG1655.10 Mucts::MueII307 | MueII307 | this work |
| MW101 | MG1655.1O Mucts::MueII101 | MueII101 | this work |
| MW315 | MG1655.10 Mucts::MueII315 | MueII315 | this work | elements contained on plasmids are listed.
Abbreviations:
fwd = forward;
rev = reverse.;
Ap$^r$ = ampicillin resistance,
Tc$^r$ = tetracycline resistance,
Cm$^r$ = chloramphenicol resistance.

EXAMPLE 2

Construction of New Polylinker Mini-Mus

The commonly used MudII4041 (Castilho, Olfson et al. (1984). J Bacteriol. 158: 488–495.) has an open reading frame extending only into the element and a BamHI site for cloning genes in. In addition, there are 118 base pairs (~40 amino acids) at the end of the element which are incorporated into every fusion product. We have engineered new elements with polylinkers and open reading frames both into and out of the elements, and with as few as 58 bp (~20 amino acids) at the end incorporated into fusion products which still retain transposition levels high enough for use in an in vivo Protein Fusion system.

Shortest Mu end sequence and insertion of polylinkers. Several deletions at the Mu right end were obtained and analyzed. Plasmid pBC4041 was digested with BamHI and Bal31 deletions were made extending various lengths into the end of Mu. The DNA was then digested with HincII and religated with an EcoRI linker to connect the deleted Mu right end to a uniform site inside the Mu. The DNA was transformed into a Mu lysogen and a number of clones were isolated, and the deletion length and sequence was determined. Except for the deletion which only retained 18 bp or the Mu attR, these elements had reported transposition frequencies with less than a 10-fold decrease in transposition from the parental mini-Mu, MudII4041 (containing 118 bp of the right end). A summary of open reading frames extending through each of the different Mu elements is depicted in FIG. 2 SEQ ID NOS. 3 and 13.

A polylinker sequence was synthesized for incorporation into the element to facilitate domain cloning into each of the elements. The sequence described in FIG. 1 is one such polylinker sequence SEQ ID NOS. 1 and 2. It was designed to include a series of restriction sites which would be unique in the Mu element. In addition, it was designed so that unidirectional deletions into an inserted domain could be generated with the exoIII exonuclease (Henikoff. (1987). Meth Enzymol. 155: 156–165.), a potentially useful feature to combine in vitro techniques with in vivo protein engineering techniques. The polylinkers were inserted in both orientations into three Mu deletion elements to create pIVP311–316 as shown in FIG. 1.

Figure 2:
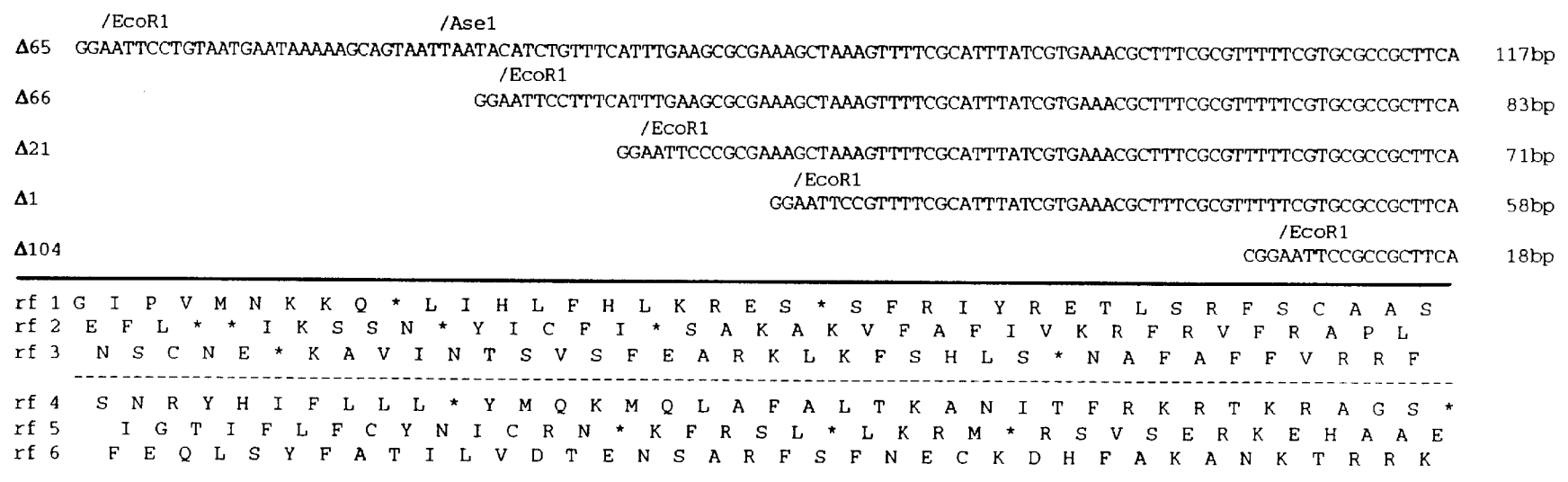

FIG. 1 depicts maps of polylinker mini-Mu elements constructed. a) MudII4041 is the parent of all mini-Mu derivatives described. b) Mini-Mu deletion elements deleted for various lengths at the right end of Mu (see FIG. 2). BamHI IS replaced with an EcoRI site. c) New mini-Mu elements derived from the deletion elements. These new elements contain polylinker sequences inserted into the EcoRI site. Polylinkers were synthesized by making the two oligonucleotide sequences shown, hybridizing, and filling-in with DNA Polymerase I Large (Klenow) Fragment. The synthetic polylinker sequences were inserted into the filled-in EcoRI sites of MudII4041Δ66, MudII4041Δ21, and MudII40401Δ1 and isolated in both orientations. The resulting Mu elements were named pIVP311 (Δ66 Kpn . . . Nru), pIVP312 (Δ66 Nru . . . Kpn), pIVP313 (Δ21 Kpn . . . Nru), pIVP314 (Δ21 Nru . . . Kpn), pIVP315 (Δ1 Kpn . . . Nru), and pIVP316 (Δ1 Nru . . . Kpn). Polylinker sequences were designed to contain no stop codons.

FIG. 2 depicts Mini-Mu elements with Deleted ends SEQ ID NOS. 3–13. The right ends of the five deleted mini-Mu elements (MudII4041Δ65, MudII4041Δ66, MudII4041Δ21, MudII4041Δ1, and MudII4041Δ104) are displayed. Elements were constructed by digesting MudII4041 with BamHI, performing a Bal31 treatment digesting with HincII to give them a common left side and religating with an EcoRI linker to give the sequences shown. The amount of attR remaining is shown on the right side. Translated sequences extending through these elements are shown on the bottom of the figure.

Analyzing transposition and transposition frequency. Since these elements had deleted and altered ends, their transposition frequency was determined in a mating-out assay (Darzins, Kent et al. (1988). Proc Natl Acad Sci, USA. 85: 6826–6830.) to assess if transposition was high enough to be useful in the in vivo protein engineering applications. A mating-out assay is performed by observing transposition of the mini-Mu elements (containing a marker for kanamycin resistance) into a deleted F' carrying a marker for tetracycline resistance (F'tet). MG1655.10 cells (recA, no δγ transposon) harboring both the F'tet and a plasmid carrying the transposon of interest (the original deletion mini-Mus on plasmids pNEKΔ65, pNEKΔ66, pNEKΔ21, pNEKΔ1, pNEKΔ104, or the new polylinker mini-Mus pIVP311–316) were diluted 1:50 and grown for 2 hours at 37° C. to induce transposition. The cells were mated to M8820 Mucts and plated onto media containing streptomycin to select against the donor, and either tetracycline or both tetracycline and kanamycin. Transposition into the F'tet was determined as a ratio of Tc$^r$Ap$^r$/Tc$^r$ cells since the cells which were Ap$^r$ had a copy of the pIVP plasmid transposed as a cointegrate structure into the F'tet. Levels of transposition for most of the elements tested (MudII4041, MudII4041Δ65, MudII4041Δ66, MudII4041Δ21, MudII4041Δ1, MueII311–316) were approximately $1 \times 10^{-5}$. Only the MudII4041Δ104 element containing only 18 bp of the Mu right end had no appreciable transposition. These numbers are typical Mu transposition numbers and give more than enough independent insertion events for random protein fusion purposes.

New element structure. The new mini-Mu elements developed contain several useful features. One of the elements is summarized in FIG. 3 SEQ ID NOS. 15–20. The new elements have open reading frames extending in both directions, convenient polylinker sequences at the end for cloning in protein domains and performing in vitro directional deletions with exoIII, and transpose at high enough frequencies to be used in the system. The DNA sequence of the new mini-Mu element consisting of a left end (attL), a polylinker, and a truncated right end (attR) is shown in FIG. 14 SEQ ID NO. 24.

FIG. 3 shows example reading frames and restriction sites of the new polylinker Mu elements. The open reading frames both into and out of the right end of one of the new Mu elements is depicted for pIVP315 (a Δ1 derivative). These new elements provide a versatile set of tools for cloning in domain sequences. The Mus based on the Δ1 elements allow a restriction site to access two reading frames extending out of the element, and the Δ21 derivatives (not shown) allow the restriction site to access the third. The same holds true for fusions extending into the elements except that only two of the reading frames defined by a given restriction site are accessed. →: Open reading frames (ORFs) extending out of the element; ←: Open reading frames extending into the element; XXX: closed reading frames.

EXAMPLE 3

Method for Construction of Carboxy-Fusions (Fusions Extending Out of the Elements)

Carboxy-terminal fusions. Carboxy-terminal fusion elements are useful for a number of applications including the fusing of activities, promoters, and other elements to the amino-end of a cDNA cloned gene which is missing regulatory components, or for generating fusion elements using proteins which only prefer fusions at their carboxy-end. Due to lack of an open reading frame running out through the end of the commonly used Mu transposable elements, it was not possible to construct carboxy fusions before the generation of the constructs of the instant invention. This example and the following results demonstrate that: A Protein A gene could be functionally cloned into the right end of Mu with the translational reading frame oriented out of the element; transposition of the new Protein A Elements occurred at high levels and generated both transcriptional and translational fusions at the expected frequencies; translational fusions were distributed randomly over the target gene; fusions were generated and isolated with both a selectable and a screenable gene; and functional fusion proteins which retained activity in both fused domains could be obtained.

Cloning Protein A into Mu. A synthetic Protein A domain was cloned into the polylinker of the Mu element contained on pIVP315 as outlined in FIG. 4. The Not I to BamHI fragment containing the carboxy-end truncated Protein A domain from pEZZ18 (Pharmacia) was cloned into the BamHI site of pIVP315. In order to generate the proper fusion extending out of the Mu element, the BamHI of both the vector and the insert were made blunt by a filling-in reaction with Klenow fragment. Several hundred transformants were screened by colony hybridization using the GENIUS non-radioactive detection kit (Boehringer Mannheim) using the manufacturers instructions and eleven tested positive for the Protein A. Of these eleven candidates, two were found which had the Protein A fragment in the proper orientation (pMW101 and pMW102).

The first clone, pMW101, was identified as having two direct repeats of the Protein A fragment leading out of the element. The second clone, pMW102, was identified as having two direct copies of the vector and a single copy of the Protein A gene leading out of one of the two Mu elements which had been formed on this plasmid. pMW102 generated spontaneous deletions which reformed the original pIVP315 vector. This is one of the two possible products of a homologous recombination between the two directly repeated copies of the vector. We were able to prevent the recombination event by transferring the recombinant plasmid to a recA⁻ strain (M8820TR Mucts). pMW101 contained a fusible copy of the Protein A gene and an extra non-fusible internal copy of the Protein A gene which was useful as a control.

Figure 4:
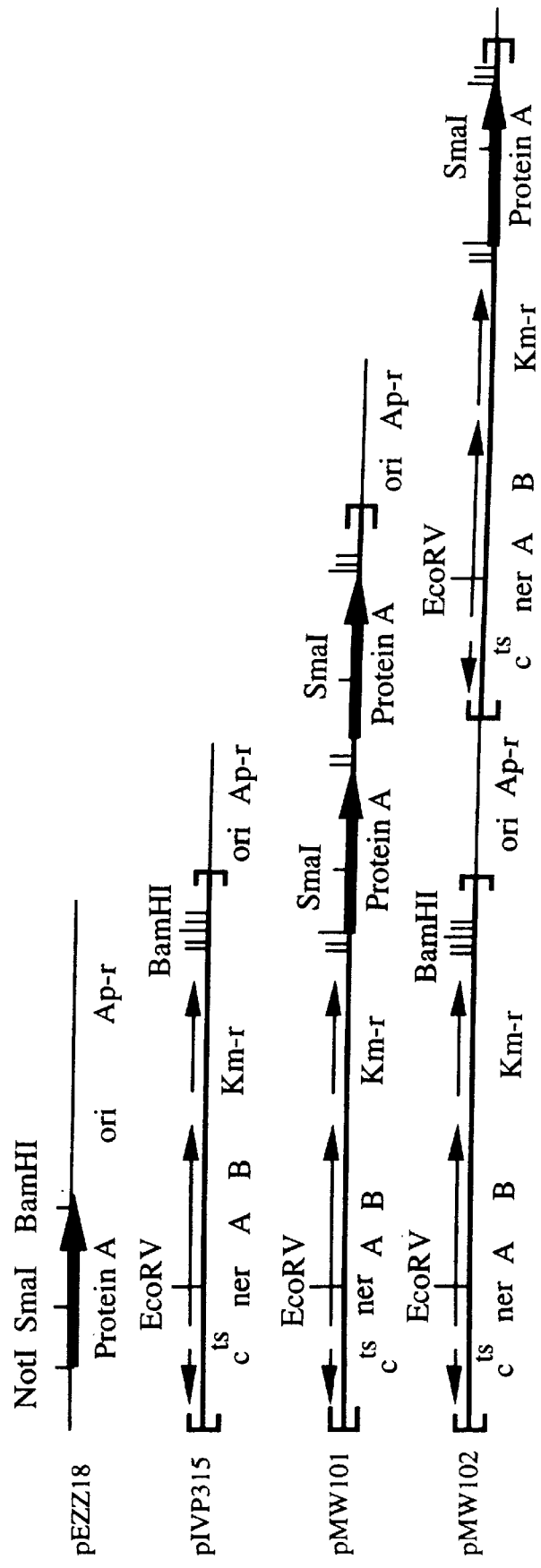
FIG. 4. Construction of pMW101 and pMW102.

FIG. 4 describes construction of pMW101 and pMW102. The synthetic Protein A gene from the plasmid pEZZ18 (Pharmacia) was cloned into a filled-in BamHI site in the polylinker of pIVP315 as a NotI-BamHI fragment which had been made blunt by filling-in. pMW101 contained two tandem copies of the Protein A and pMW102 contained two tandem copies of the vector sequence.

Testing transposition frequencies of the MW101 Protein A fusion element. A test whether the new elements maintained their transposition frequency showed that the new element transposed at approximately the same levels as the parent.

Putting the Mu elements into the chromosome. The Protein A element was transposed into the chromosome of MG1655 Mucts so that any plasmid containing a gene of interest could be used as a target. MueII101 and MueII315 (the parental Mu without Protein A) were transposed into the chromosome of MG1655.10 Mucts (a recA-, δγ- strain with a Mucts62 helper phage). A lysate of MC1040-2 harboring a plasmid containing the desired transposon was made and used to infect MG1655.10 Mucts. After adsorption, the cells were plated on YT media (Miller. (1972). .) containing 12 μg/ml kanamycin to select for the mini-Mu elements and transductants were picked and tested for loss of the ampicilin resistance present on the initial plasmid. This ensured that the mini-Mu element had transposed into the chromosome. Strains were isolated for further use: MW101 which contained a chromosomal insertion of MueII101; and MW315 which contained a chromosomal insertion of MueII315.

Figure 5:
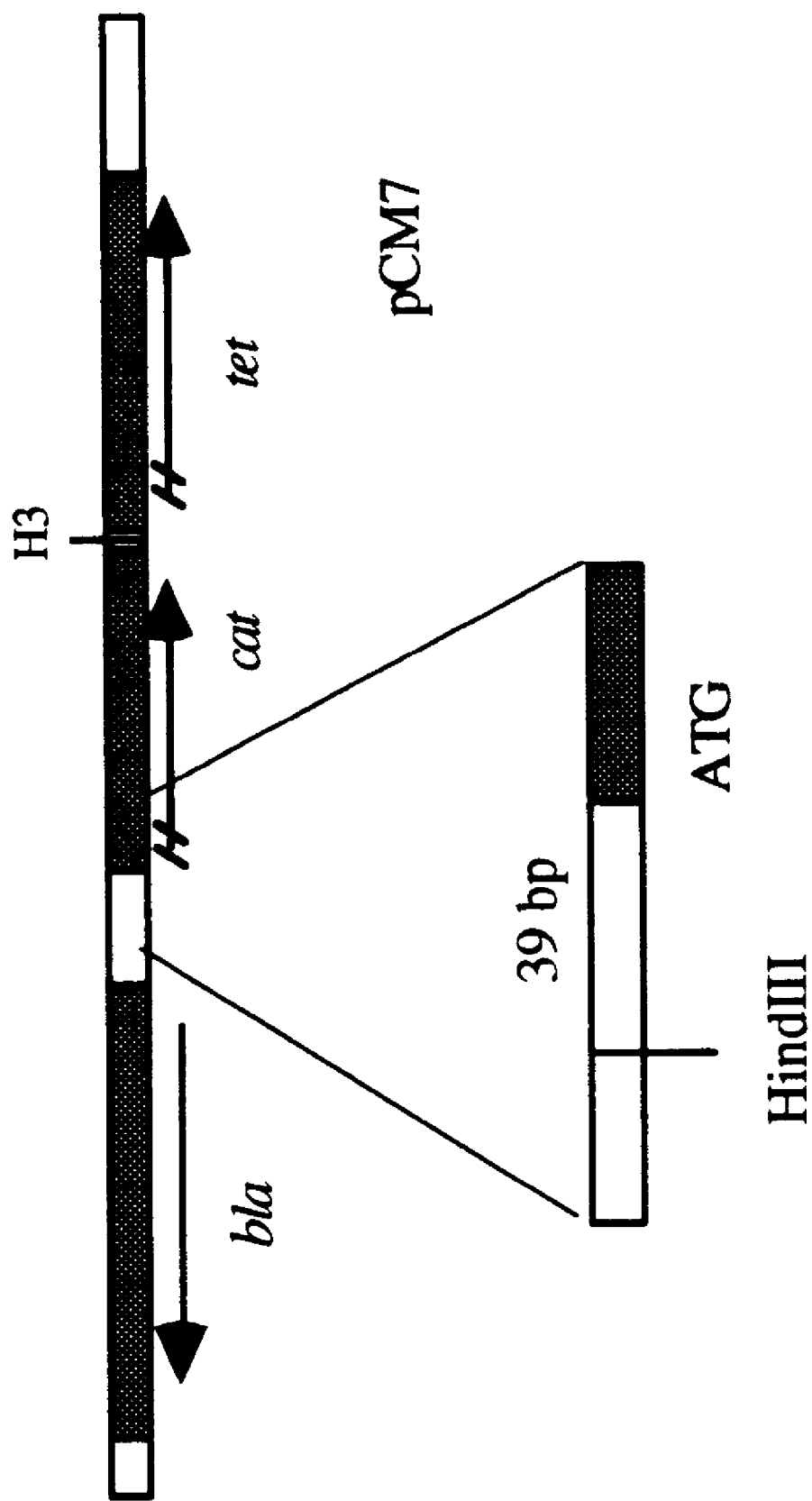
FIG. 5. Translational Target and map of pCM7.

Plasmid pCM7 (Pharmacia) was initially used as the target plasmid (see FIG. 5). This plasmid was a derivative of pBR327 and contained a selectable ampicillin resistance gene, a promoterless chloramphenicol-acetyl-transferase gene, and a promoterless tetracycline resistance gene (The tet promoter had been completely inactivated by insertion of the cat gene into the HindIII site).

Plasmid transduction experiments were carried out to demonstrate that the new element exhibited sufficient transposition levels for use in an in vivo protein engineering system. MW101 (containing the MueII101 element in the chromosome) which harbored the target plasmid pCM7 was induced for transposition and the lysate was used to infect M8820 Mu cts cells to isolate single insertion events. Plasmid transductants were identified as being ampicillin resistant and were tested for resistance to kanamycin coded by the transposon. We were able to isolate approximately 1000 independent transposition events per ml of lysate used. This number is sufficient when scaled to larger quantities to saturate a 4–10 kb plasmid with insertions. Restriction analysis of plasmid DNA from the transductants showed that the plasmids contained the MueII101 element as predicted and that the mini-Mu elements were randomly distributed around the plasmid by observing a range of different restriction patterns.

Creation of translational fusions. Experiments were performed to determine what proportion of activated target genes would need to be screened in order to find a translational fusion. If the gene was missing the start codon, a very significant proportion of activated target genes should be translational fusions. However, to make this system even more versatile, it desirable to have to screen only a few transductants if the target is, for example, a cDNA clone which is missing the promoter but has a start codon.

We define an area called the "translational target" covering the region of the target molecule which can potentially form a translational fusion if appropriately used by the fusion element. The translational target extends from the first in-frame stop codon upstream of the target gene to an unknown position within the target gene itself which can still make active fusions. Fusions within this area have approximately ⅓ chance of making an active translational fusion with the target gene due to reading frame considerations. The relative frequency should be significantly higher if the target gene is a cDNA clone which does not contain a good Shine-Delgarno sequence (Shine and Delgarno. (1974). Proc Nat'l Acad Sci, USA. 71: 134–246.) since most activating events will be translational fusions.

The target plasmid pCM7 gave an good analytic approach to studying the translational target of the cat gene since the HindIII site upstream of the gene was exactly inside the first stop codon in frame with the ATG of the cat gene (FIG. 5). Insertions that activated chloramphenicol resistance which mapped within the HindIII fragment of pCM7 were within the translational target. This site was 39 bp upstream of the ATG codon, thus defining a translational target that was at least 39 bp long. Of the 80 insertions selected on chloramphenicol media which were screened, two mapped within this fragment (about 2.5%). If the "transcriptional target" extended 1 kb upstream of the cat gene (the insertion which mapped furthest away from the ATG) then the frequency one would expect a random insertion which could activate cat to go into this region is about 39 bp/1000 bp=3.9%. This, of course, assumes that the translational target does not extend very far into the gene.

Figure 6:
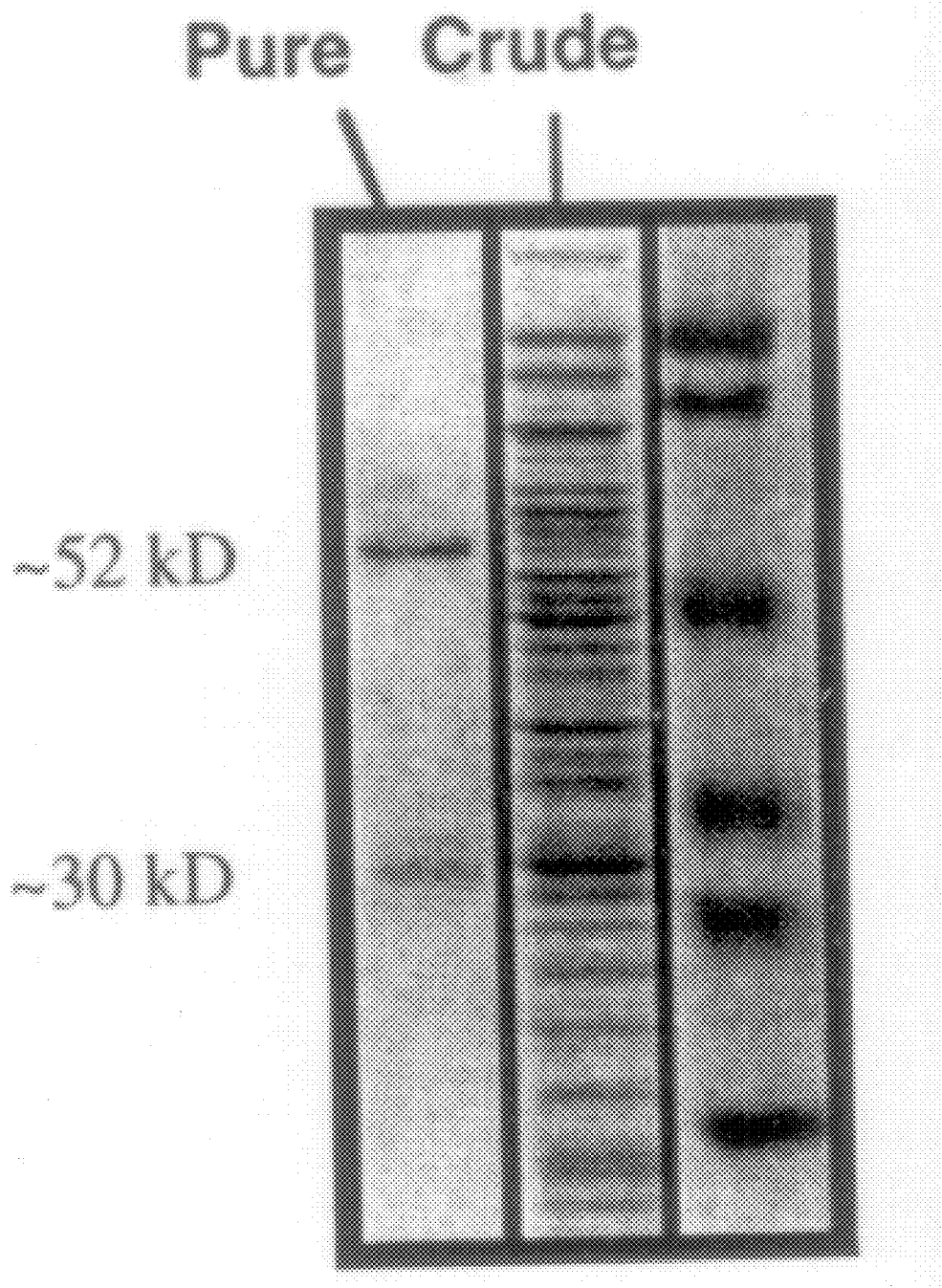
FIG. 6. SDS PAGE analysis of potential Protein A fusion protein.

Target plasmid pCM7: Selectable CAT gene fusions. The potential fusions were isolated in the previous section were analyzed. Both insertions appeared to map extremely close to the ATG of the cat gene. We processed fusion candidate 13L further to verify fusion. A protein extract was prepared and purified over an IgG affinity matrix (Pharmacia) to purify the Protein A species which should be fused to chloramphenicol-acetyl-transferase. An SDS polyacrylamide gel was run and the results are shown in FIG. 6.

We see two bands on the gel as predicted for a fusion product: one for the fusion product, which we have calculated approximate molecular weight of about 52 kD, and one for a Protein A product which is produced from the internal copy of the Protein A gene in MueII101.

Target plasmid pMC1871: Screenable β-galactosidase fusions. Plasmid pMC1871 contains a promoterless, truncated lacZ gene which was missing the first eight codons of the β-galactosidase gene. It is widely used as a plasmid for creating translational fusions with lacZ since the β-galactosidase enzyme is missing the first eight amino acids and can only be activated through translational fusion with another gene. After using a selection scheme for generating fusions, we wished to use the promoterless, ATG-less gene as a target to assess the frequency and randomness of making translational fusions with the new Mu element in a screening process.

MW101, and MW315 were transformed to tetracycline resistance with monomers of pMC1871 and transposition was induced. The lysate was used to infect M8820Muts and plasmid transductants were selected by plating onto LB media with 20 μg/ml kanamycin and 10 μg/ml X-gal. This selected for plasmids which had Mu insertions and allowed us to screen for activation of β-galactosidase through a protein fusion event. We isolated blue fusion colonies at a frequency of 0.5% (about 1 in 200).

Five potential fusion isolates (IVP321–325) were chosen, only four of which were viable upon restreaking. The nonviable isolate (IVP325) was very dark blue on the X-gal plate and grew very slowly. This isolate may have produced a lethal fusion protein. Plasmid DNA was prepared from these isolates and the location of the Mu insertions were mapped using restriction analysis. The location of the insertions with Two of the insertions (IVP321 and IVP324) map outside of the translational target, implicating a transcriptional, not translational, fusion was formed (probably with the fortuitous ATG shown in FIG. 7). Isolates IVP322 and IVP323 were potentially translational fusions. Western analysis (Walker. (1986). Experiments in Molecular Biology. 171–178.) was performed by running cell extracts from IVP321–324 on a 6% Polyacrylamide SDS gel, blotting to nitrocellulose, and using a monoclonal antibody against β-galactosidase (Boehringer Mannheim) to probe for the β-galactosidase domains. Isolate IVP323 had a β-galactosidase protein larger than native β-galactosidase. The size of this protein roughly corresponded to the predicted size of a Protein A and β-galactosidase fusion (about 135 kD). Isolate IVP322 was not a protein fusion. The Mu element may not have inserted into a site which fused the reading frame of the Protein A gene with the reading frame of the lacZ gene, but had somehow picked up a fortuitous ATG. Alternatively, the fusion event may have been made, but the fusion protein was unstable and yielded a degradation product. No breakdown product was seen in any appreciable concentrations from IVP323 indicating that it yielded a stable fusion product. This is evidence that the short protein linker which is inserted between fused domains from the end of the mini-Mu allows production of a stable protein fusion.

FIG. 5 shows a Translational Target and map of pCM7. Translational target of pCM7 is defined by the HindIII fragment. The HindIII site upstream of the ATG of cat cuts just before the first upstream stop codon in frame with the ATG. Mu insertions into this fragment activated the cat gene from the right end of Mu.

FIG. 6 shows SDS PAGE analysis of potential Protein A fusion protein. SDS polyacrylamide gel showing purified Protein A species from sample 13L. Lane 1) IgG purified extract of potential fusion sample 13L. Two major bands are seen with molecular weights of about 52 kD and 30 kD. These bands are consistent with the expected bands from a Protein A and chloramphenicol-acetyl-transferase protein fusion. Lane 2) Unpurified extract from sonicated 13L cells. Lane 3) Molecular weight standards (BIO-RAD prestained low molecular weight).

Figure 7:
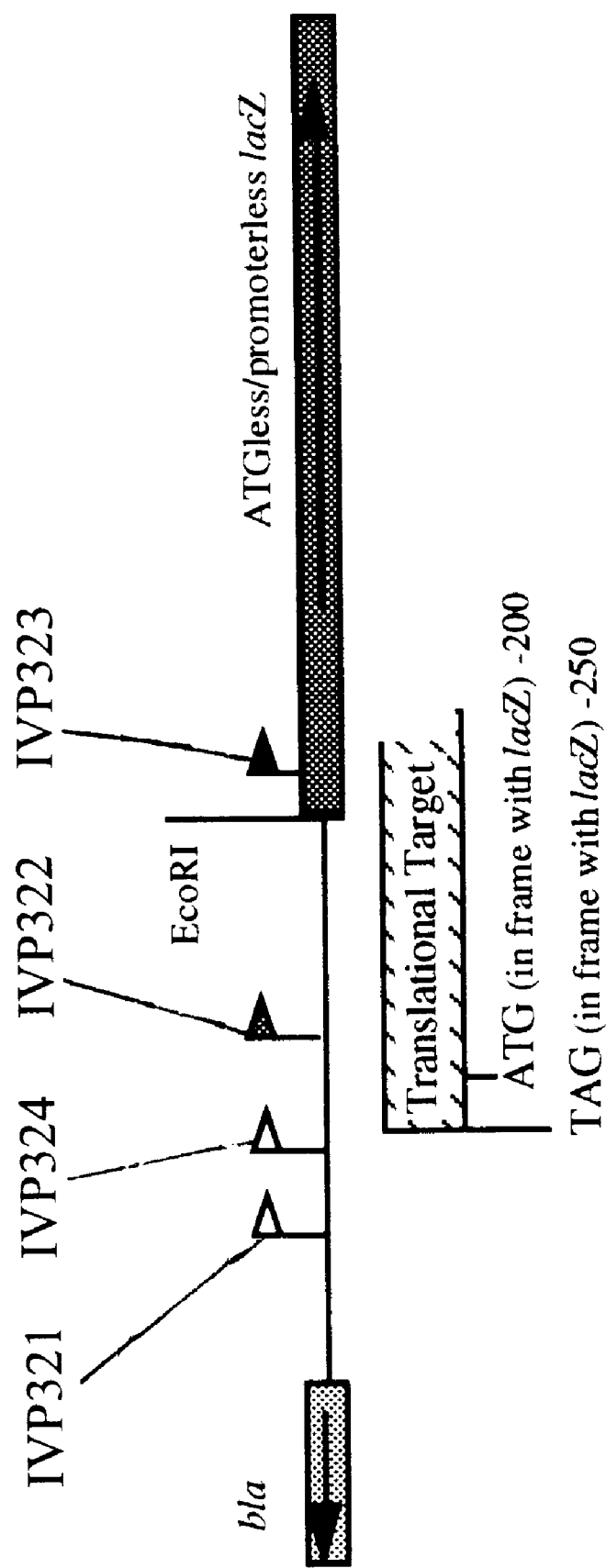
FIG. 7. Mapping fusions between Protein A and β-galactosidase.
Figure 7:
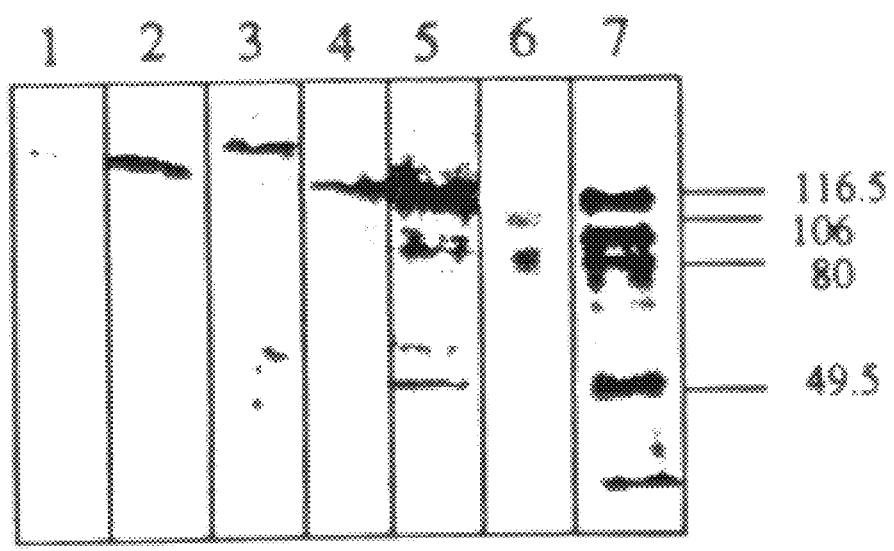

FIG. 7 depicts mapping fusions between Protein A and β-galactosidase. Insertions IVP321–324 were isolated as β-galactosidase (+). a) The insertions were restriction mapped using the Eco RI site at the right end of Mu and at the beginning of the truncated lacZ gene. The direction of the flag indicates the orientation of Mu with respect to translation of Protein A. The shades of the flags indicate relative β-galactosidase activity with black (IVP323) being the highest. b) Western analysis of extracts IVP321 (lane 1), IVP322 (lane 2), IVP323 (lane 3), IVP324 (lane 4). Control strain E5014.2 (lane 5) constitutively produces β-galactosidase. Prestained low (lane 6) and high (lane 7) molecular weight standards were obtained from BioRad. The blot was probed with monoclonal mouse anti-β-galactosidase obtained from Boehringer Mannheim. Secondary antibody was a Goat-anti-mouse Horse Radish peroxidase conjugate (BioRad).

Conclusions. The results show that Protein A fusions could be made with the new mini-Mu elements, and that these new mini-Mu elements were now capable of forming carboxy-terminal fusions by translation out of the element through an open reading frame. We overcame our initial problems with cloning Protein A by using a less lethal version of the gene. Further experiments will address the cloning of lethal genes by introducing regulatable promoters into the elements.

We also analyzed the utility of these elements. The new mini-Mus retain their high frequency of transposition even though they have a shorter right end sequence. Depending on the target, 10–1000 mini-Mu insertions can be selected per ml of lysate used. When using a pUC-like (colE1) plasmid which gives high levels of Mu insertion, we can isolate up to 100,000 random insertion events with only 100 ml of lysate.

We have analyzed the ability to make carboxy-terminal protein fusions with either a selection or a screen for the protein fusion. In the case of selection for activation of the cat gene, about 1 in 50 of the activating insertions were translational fusions. The rest were transcriptional fusions. This gene had a functional ATG and ribosomal binding site. With the β-galactosidase fusions, 1 out of 4 of the insertions which activated β-galactosidase turned out to be a translational fusion. Activating fusions were visualized on X-gal plates and occurred at a frequency of about 1 in 250. This gene had neither a functional ATG nor a ribosomal binding site. The example of β-galactosidase is analogous to a cDNA clone from a higher organism which may not have a functional promoter or adequate ribosomal binding site in E. coli.

The frequencies reported here are sufficient to generate hundreds of independent protein fusion events if desired. The system can, however, be improved by increasing the proportion of translational fusions which are made and reducing the number of transcriptional fusions which are made. We have designed features into the system which will allow this and will also incorporate a way of screening for carboxy-fusions even if the particular gene of interest has no simple screen or selection associated with its function.

Finally, two other important conclusions were reached. First we were able to make protein fusions which retained the activity of fused domains. This is important for the generation of multifunctional enzymes. One of the advantages to an in vivo system which generates large numbers of random fusions is that even if some fusion combinations are inactive or partially active, there are many more that are generated. In some cases only the good fusions will be observed. Second, we have demonstrated that the sequence at the right end of Mu which becomes incorporated into the protein fusion product is stable and allows for a stable protein product to be produced. This holds true for the one reading frame that was tested. There is a second reading frame extending out of the new Mu elements which can also be used.

EXAMPLE 4

Construction of Amino Fusions with Mu Elements (Fusions Extending Into the Elements)

Summary. Amino-terminal fusion elements are useful for generating fusions with proteins or domains which contain expression regulation information and/or signal processing domains (secretion, targeting, etc. . . . ) which are commonly found at the amino terminus of proteins. Construction of amino terminal fusion elements has been demonstrated above. This example demonstrates the feasibility of using the protein engineering system to create multifunctional enzymes. Work has been done to study what effects a random series of protein fusions between two genes may have on enzyme activity. This analysis demonstrates whether fusions to different target sequences affected enzymatic activity of the transposing domain. This example also serves to assess how easily the methods and constructs of the instant invention could generate random fusions with a target gene using a screen for the desired activity. This example also demonstrates the advantageous use of the propensity for a Mu based system to distribute insertions randomly throughout a target plasmid, and shows the generation of functional fusion proteins.

Construction of Amino-terminal fusions. A series of β-galactosidase amino terminal fusions were constructed using the mini-Mu element MudII1734. MudII1734 is a fusion element containing a lacZ gene which is truncated at the eighth codon. In order for β-galactosidase activity to be expressed, the Mu element must transpose into the proper reading frame of a target gene and fuse the lacZ gene in the proper reading frame to the carboxy end of another gene. We chose to study fusions with the tetracycline resistance gene in plasmid pBR327 and were also able to isolate fusions to the β-lactamase (ampicillinase) gene.

Screening for both activities. Plasmid pBR327 was transformed into the strain POII1734D (which contained the MudII1734 in the chromosome) and insertions were made by inducing transposition of MudII1734 at 42° C. The lysates were used to infect M8820 cells and potential fusions with the tetracycline gene were isolated by plating onto LB media with 100 μg/ml ampicillin and 10 μg/ml X-gal. We screened insertions for activity of both domains: tetracycline resistance and β-galactosidase. Potential β-galactosidase fusions were scored as blue colonies and comprised 14% of the total colonies on the plate. Of these, 58 colonies were screened for resistance to tetracycline (29 whites and 29 blues). We found that 21% of the white colonies and 14% of the blue colonies were sensitive to tetracycline (indicating an inactivating insertion into the tetracycline gene) These numbers demonstrate the utility of using a screen procedure for both activities being studied in an efficient way. A series of insertions were isolated, some of which inactivated the target gene and some of which kept the target gene's activity.

Figure 8:
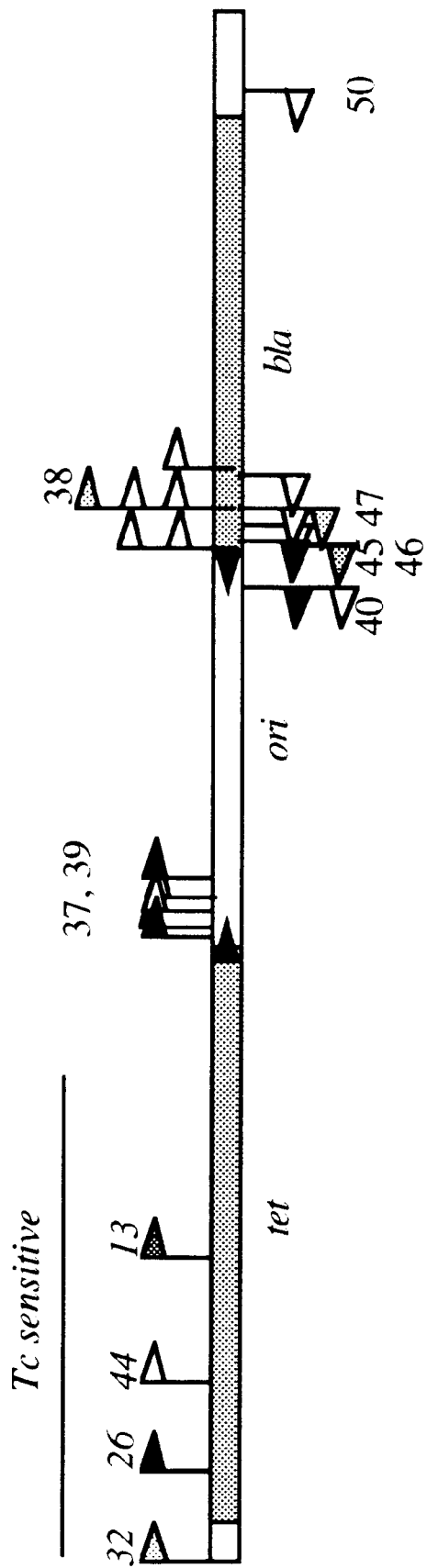
FIG. 8. β-galactosidase amino-terminal insertion sites into pBR327.

The map positions for 25 individual insertions both β-galactosidase (+) and (−) are given in FIG. 8. Insertions which activated β-galactosidase activity are designated. As can be seen, a wide distribution of insertions were obtained, with a few clustered hot-spots. A wider range can easily be obtained by isolating hundreds or thousands of such independent insertion by scaling up the lysate (100 μl of original lysate was used to generate these fusions. Several fusions with both the tet and the bla (β-lactamase) genes were obtained. Translation from fortuitous start codons just downstream of the tet and bla genes can be seen to occur. The map is predictably devoid of insertions into the bla gene (since plasmids were selected with ampicillin) and the origin of replication.

Several promoters can be used in the system. Table 2 lists a number of promoters which have been used in protein expression applications. The ideal promoter is tightly controlled, with little or no transcription in the repressed state, and a large increase in transcription when induced. Promoters which rely on temperature induction (such as versions of the lambda $P_L$ promoter) are not useful since Mu transposition is controlled by temperature induction.

TABLE 2

Regulatable promoters for the control of gene expression. A series of regulatable promotors which can be incorporated into the protein engineering system. More than one promotor can actually be engineered upstream of the gene insertion site in the carboxy-fusion mini-Mus. When combined with targets on a shuttle vector, the protein fusions can easily be transferred bewteen organisms. IPTG: isopropyl-β-D-thiogalactoside; IAA: Indole Acrylic Acid.

| Promoter | Description | Control/Inducer (REF) |
| --- | --- | --- |
| lac | lac operon promoter (Reznikoff and Abelson. (1978). The operon.) | lac repressor/IPTG |
| tac | Hybrid trp-lac promoter (DeBoer, Comstock et al. (1983). Proc Natl Acad Sci, USA. 80: 21–25.) | Lac represssor/IPTG |
| lacUV5 | Up-mutant lac promoter (Reznikoff and Abelson. (1978). The operon.) | Lac repressor/IPTG |
| ν $P_L$ | Phage ν promoter (Ptashne. (1988).) | cI (ν repressor)/temperature |
| ara | Arabinose operon promoteraraC activator/arabinose (Casadaban. (1975). Proc Nad Acad Sci, USA. 72: 809–813.) | |
| trp | trp operon promoter (DeBoer, Comstock et al. (1983). Proc Nad Acad Sci, USA. 80: 21–25.) | trpR repressor/IAA |
| T7 | Phage T7 promoter (Pagratis. (1987). Current Communications in Molecular Biology. Gene Transfer Vectors for Mammalian Cells. 5-9.) | –/T7 polymerase |
| tbg (Thermus) | thermo-β-galactosidase promoter (Demirjian, Pagratis et al. (1988). Molecular genetics of bacteria and phages: prokaryotic gene regulation. 39.) | — |
| GAL1/10 (yeast) | Galactose yeast promoter (Johnston and Davis. (1984). Mol Cell Biol. 4: 1440–1448.) | GAL4/Galactose |

FIG. 8 shows β-galactosidase amino-terminal insertion sites into pBR327. Map positions of insertions into pMC1817. A series of insertions were mapped to determine the distribution of insertions. Flags indicate direction of mini-Mu. Arrow end indicates translation of target gene into the element to make a fusion at the amino terminus of β-galactosidase. The shade of the flag represent relative β-galactosidase activity (black is highest). Plasmids containing the fusions fp13, fp26, fp32, fp43 and fp44 are all tetracycline sensitive. All cells are ampicillin resistant

EXAMPLE 5

Expression-Controlled Fusion Elements

Figure 9:
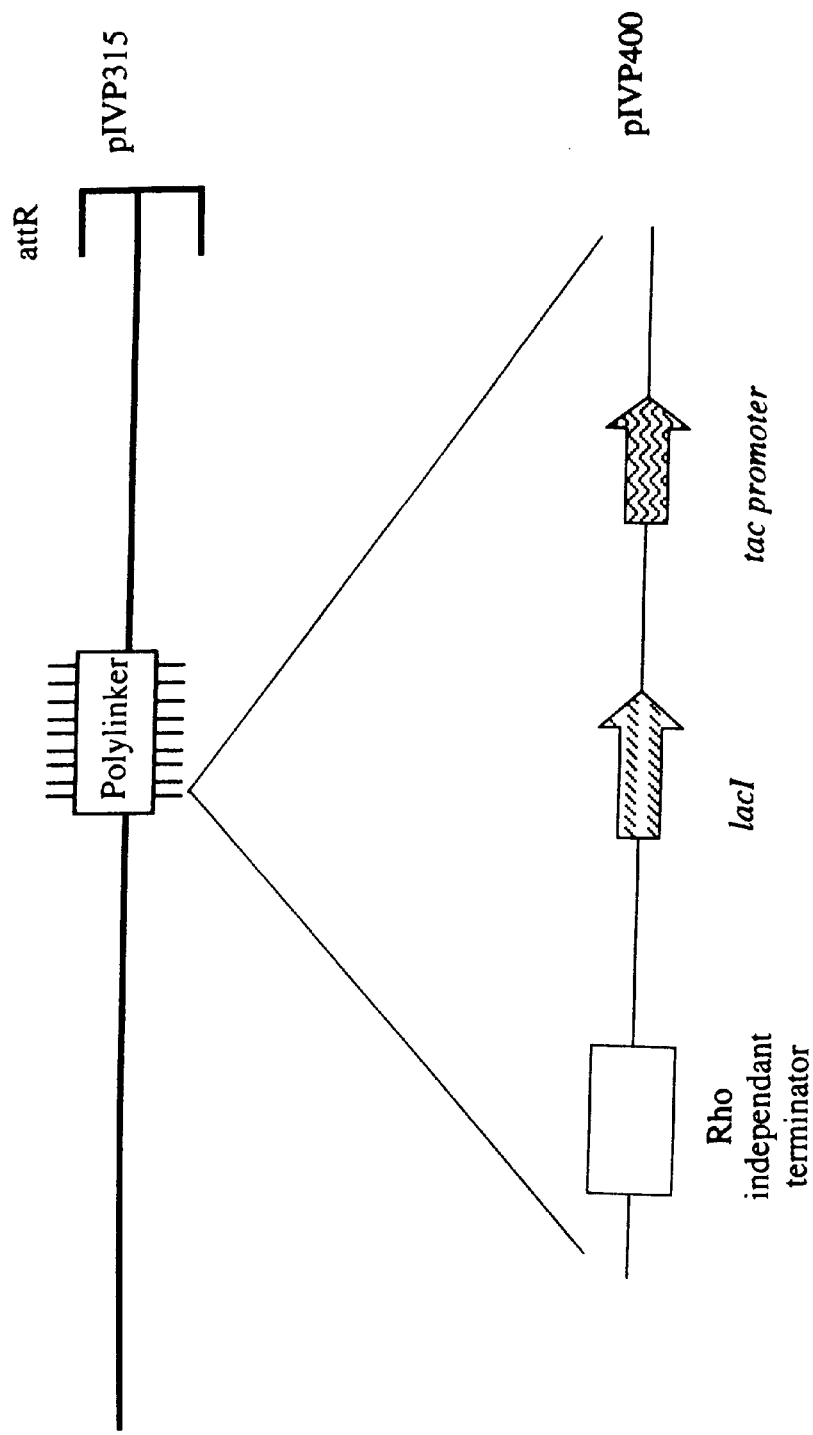
FIG. 9. Enhanced polylinker elements.

Features that are described in this section are summarized in FIG. 9 and include:

Adding regulatable promoters to carboxy-terminal elements. We have added a promoter which allows control of transcription for lethal genes, increase of fusion product production, and expression of genes from a number of different organisms. The promoter is especially useful for the carboxy-terminal fusion elements.

We chose a promoter that was controlled by the lac repressor which is convenient because of its induction with IPTG (DeBoer, Comstock et al. (1983). Proc Natl Acad Sci, USA. 80: 21–25.) The lacI (repressor) gene was engineered internally into the transposon so that it is carried with it into a new strain. A DNA fragment which contained the lacI gene and the tac promoter was amplified from plasmid pMAL-p (New England Biolabs) using the polymerase chain reaction (Saiki, Gelfand et al. (1988). Science. 239: 487–491.). During the amplification process, the trp transcriptional terminator sequence was added upstream of the lacI gene to prevent read-through transcription from inside the Mu element. The amplified fragment was cloned as a KpnI - EcoRI fragment into the polylinker region of pIVP315. FIG. 9 depicts the structure of the element which was created. FIG. 13 depicts the sequence of the primers which were used in the amplification reaction.

Other promoters are also commercially available for use in this system. The trp promoter can be cloned as a HindIII to BamHI fragment from plasmid pDR720 (Pharmacia). The T7 promoter can be cloned from a number of sources such as pBluescript$_{II}$ KS+ plasmid (Stratagene) as a BssHII-EcoRI fragment. They cab be cloned into the Mu elements by insertion either into the polylinker sites or into the BstBI site just after the end of the kanamycin resistance gene of the mini-Mu elements. The promoters are tested by making random fusions to a target gene such as the promoterless cat gene on pCM7. Expression from the trp promoter will be monitored in a trpR$^+$ (repressor) strain such as C600. Induction of the trp promoter can be achieved by addition of Indole Acrylic Acid (IAA). Expression from the T7 promoter will be achieved by isolating the insertions into BL21 (DE3) cells which contain the T7 polymerase. Expression of the polymerase is controlled by a tac promoter and is induced by adding Isopropyl-β-D-thiogalactoside (IPTG) during exponential growth of the cells (Davanloo, Rosenberg et al. (1984). Proc Natl Acad Sci, USA. 81: 2035–2039.).

A complete promoter system can be expanded by engineering promoters from organisms other than *E. coli*. If the fusion product is on a shuttle plasmid, it can be transferred to a new organism. Eukaryotic promoters such as the yeast GAL1/10 regulated promoter or the animal cell SV40 virus promoter will be extremely useful tools for production of glycosylated proteins, or other proteins which need to be expressed in an eukaryotic system. These promoters can be engineered alongside the *E. coli* promoters we will initially incorporate into the system.

FIG. 9 depicts a transposable element with a regulatable promoter inserted. A regulatable tac promoter was inserted into the polylinker region of pIVP315. The inserted fragment was amplified by PCR from pMAL-c (New England Biolabs) using the primers shown in FIG. 13. The amplified fragment contains a Rho independent terminator sequence which was added on as part of one of the primers, the lacI repressor gene, and the tac promoter. The fragment was cloned as a KpnI-EcoRI piece into the KpnI-EcoRI sites of pIVP315. The tac promoter is regulated by the lacI repressor which can be controlled with the addition of IPTG.

FIG. 13 depicts the synthetic oligonucleotide sequences used as primers to amplify the controlled promoter from plasmid pMAL-p (New England Biolabs) SEQ ID NOS. 22 and 23. Sequence MALPI-L contains a KpnI site, a trp transcriptional terminator sequence (the second set of lower case letters "gccc . . . cttttttt") and a sequence homologous to the upstream region of the lacI repressor gene. Sequence MALPI-R contains an EcoRI site and a sequence homologous to the downstream region of the tac promoter.

EXAMPLE 6

Micro-Mu Fusion Elements

The transposase genes internal to the element can pose restrictions on the use of the Mu in some applications where growth at 30° C. is limiting. Transduction into a new strain requires a Mu lysogen expressing the Mu repressor to suppress transposition upon entering the cell. The repressor is a temperature sensitive repressor and transposition may be induced at 42° C. All fusions generated need to be grown at 30° C. to prevent unwanted transposition. Most of the genes which code for thermostable enzymes have activity that is often enhanced and easier to observe at 42° C. when put into *E. coli*. Under these conditions, the Mu transposition proteins would be induced, causing cell death. If the transposition genes were removed from the elements, the insertions can be isolated into a non-Mu lysogen.

Figure 10:
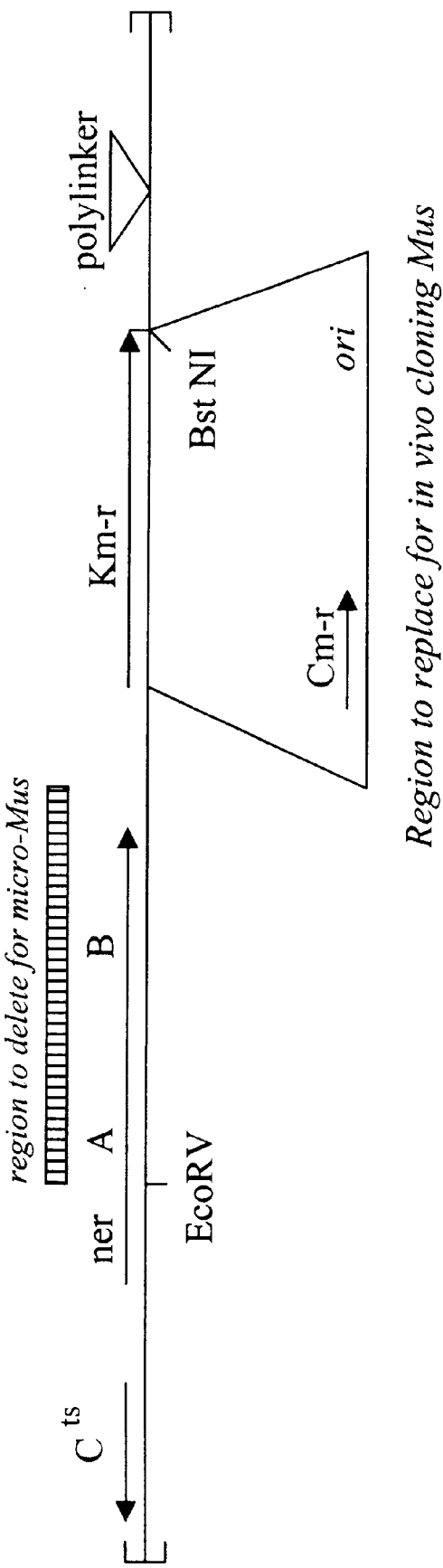
FIG. 10. Construction of micro-Mus and in vivo cloning Mus.

Mini-Mu elements without the transposition genes, sometimes called micro-Mus, have previously been described which avoid these problems (Symonds, Toussaint et al. (1987). *Phage Mu*.) Transposition is initially provided by the helper Mu present in the strain that transposition is carried out in. Insertions into a target plasmid can then be isolated by transduction into a non-Mu lysogen host, thus removing the requirement for 30° C. growth. Previous micro-Mu elements which have been constructed have shown reduced levels of transposition. This has recently been postulated to be due to the removal of the internal operator site in Mu which binds Mu transposase (Leung, Teplow et al. (1989). Nature. 338: 656–658.). New micro-Mu elements are constructed based with our polylinker-Mus using the EcoRV site just before the Mu A transposition gene and deleting to a site just before the kanamycin gene (FIG. 10). These elements will retain the internal operator site in order to prevent a reduction in transposition.

FIG. 10 shows construction of micro-Mus and in vivo cloning Mus. Micro-Mus are constructed by deleting the Mu A and B transposase proteins. Expression of these genes is controlled by the temperature sensitive Mu c repressor and the ner anti-repressor. The removed transposition genes can be complemented by a helper Mu in trans, and will allow insertions to be isolated into non-Mu lysogen strains at higher temperatures.

EXAMPLE 7

In Vivo Cloning/Fusion Elements

A technique has previously been developed by Groisman and Casadaban (Groisman and Casadaban. (1986). J Bacteriol. 168: 357–364.) for randomly cloning genes using a Mu element. This is done using the generalized transduction ability of mini-Mu elements containing an origin of replication and a selectable marker between the two ends. The high frequency of Mu transposition allows two insertion events near each other, to be packaged together with the intervening sequence. When transduced to a recA$^+$ cell, the two Mu elements can recombine with each other to generate a circular piece of DNA which now has an origin of replication (within the Mu) and the intervening sequence. The host range of Mu allows genes to randomly be cloned in this fashion in a number of enteric bacteria The mini-Mu protein fusion elements can be engineered to contain an origin of replication. These fusion elements allow a domain of interest to be inserted into the mini-Mu which can then be randomly fused throughout the genome of an organism which supports Mu growth, or into an organism containing a gene bank from another organism. Without an origin of replication, the protein fusion transposable elements can be used to randomly fuse into the genome of an organism or into a clone bank and the desired activities can later be cloned out of the chromosome. With an origin of replication in the protein fusion transposons, protein domains from the entire genome can be fused and isolated into a new host in a single step, using a selection or screening activity to assay for successful fusion which will be isolated onto a high copy plasmid. Protein domains can be cloned randomly and the desired activity can be isolated.

In vivo cloning/fusing Mu elements are constructed as shown in FIG. 10. An origin of replication will be inserted into the Mu sequence. The 1900 bp BstBI fragment from plasmid pACYC184 is inserted into the mini-Mu element. This fragment contains the cat gene encoding resistance to chloramphenicol and the p15A replicon, but deletes most of the extraneous sequences and the large tet gene.

FIG. 10 also depicts construction of in vivo cloning Mu elements. Mu elements capable of in vivo cloning are constructed by adding an origin of replication as shown in the figure. The kan gene can be replaced with the cat gene for chloramphenicol selection and an origin of replication from pACYC184. Micro-Mus capable of in vivo cloning are constructed by combining this scheme with the deletions to form the micro-Mu elements.

EXAMPLE 8

New Vectors to for Cloning Target Sequences

To increase the probability of generating translational fusions a specialized target plasmid can be employed. This is especially useful when generating insertions with the carboxy-terminal fusion element since transcriptional gene fusions can be generated if fortuitous start codons are available.

Plasmids for use with carboxy-terminal fusion elements. Construction of an optimized target plasmid is described in FIG. 11. The plasmid contains a terminator sequence upstream of a cloning site for target sequences to prohibit transcription into the target gene from upstream transposon insertions.

This plasmid additionally has an extended translational target region which can be used to form gene fusions with. A 400 bp region containing no stop codons can be inserted between the terminator and the polylinker. This extends the potential translational target of many genes which are cloned into the target plasmid. One third of the insertions into this region will be a translational fusion with the target gene of interest, assuming that the sequence which has been cloned in has no stop codons in frame upstream of the ATG. This plasmid will be most useful for working with genes which have been studied well enough to know where the start codon is. The gene can be cloned into the polylinker knowing that there are no stop codons in-frame upstream.

Figure 11:
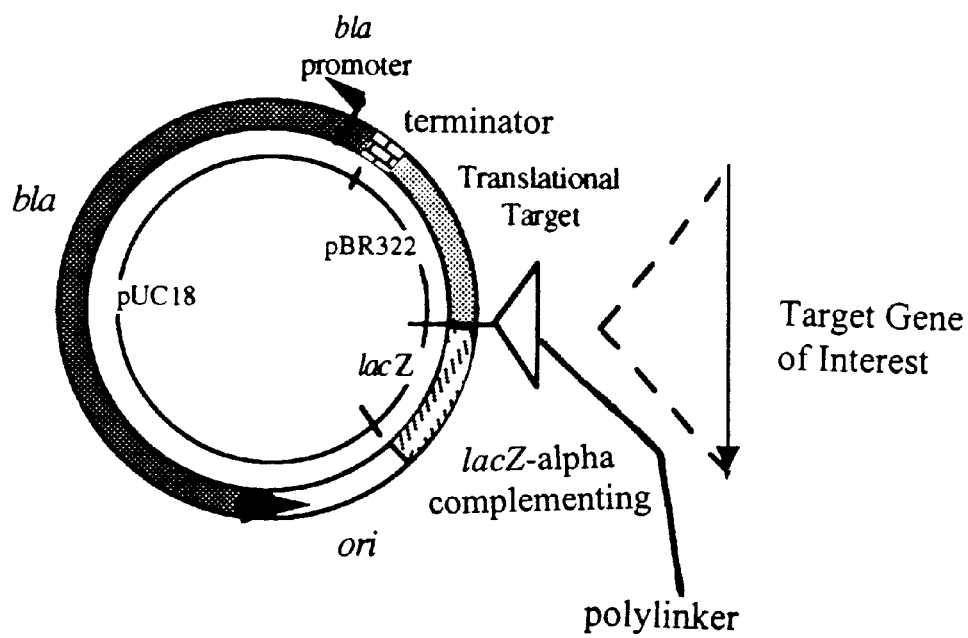
FIG. 11. New plasmid for cloning target sequences SEQ ID NO. 21.

The target plasmid is based on pUC18 and is constructed as follows: The blunted 1276 bp Aat II to Tfi I fragment from pUC18 containing the bla (ampicillinase) gene and origin of replication will be ligated to the blunt lacZ' sequence as described in FIG. 11 SEQ ID NO. 21. A synthetic translational terminator (Pharmacia) is cloned into the EcoRV site, and a synthetic polylinker sequence (FIG. 11) is cloned into a blunted EcoRI site. In addition, the 400 bp translational target described in FIG. 11 is cloned into the EcoRI-SacI site of the polylinker. This fragment is from pBR322, or equivalent sequence, and contains sequences which are normally found in the tet gene. There is only one stop codon in all three of the applicable reading frames. This stop codon will be eliminated by in vitro mutagenesis.

FIG. 11 shows a plasmid for cloning target sequences. This improved target plasmid makes the generation of translational fusions easier. The target plasmid is based on pUC18 and is constructed as follows: The blunted 1276 bp Aat II to Tfi I fragment from pUC18 containing the bla (ampicillinase) gene and origin of replication can be ligated to a PCR amplified sequence containing a synthetic translational terminator, an extended translational target sequence with few or no start or stop codons (such as a 400 bp fragment which exists in pBR322), and a synthetic polylinker sequence. A fragment from pBR322 can be used which contains sequences normally found in the tet gene. There is only one stop codon in all three of the applicable reading frames. This stop codon can be eliminated by in vitro mutagenesis. PCR primers will be engineered to contain a transcriptional terminator and homologous sequences to the translational fusion sequence on one side and the polylinker sequence depicted with homologous sequences to the translational fusion sequence on the other side.

We claim:

1. A Mu-like transposable element for generating functional fusion proteins after insertion into a target DNA, comprising
   a left transposable element attachment site attL and a right transposable element attachment site attR, wherein said right attachment site attR is no more than 62 DNA nucleotides in length, and
   wherein located between attL and attR is a site for insertion of an exogenous DNA sequence encoding for a protein domain;
   said exogenous DNA sequence, once inserted, being located within said insertion site such that after insertion of said transposable element into a target DNA sequence a mRNA sequence is transcribed from the transposable element continuous with a mRNA sequence transcribed from the target DNA sequence as a single mRNA transcript;
   wherein said mRNA transcript may originate from the target DNA or from the transposable element;
   such that said mRNA transcript may originate from target DNA on either side of the transposable element, and continue through at least one end of the transposable element, either attL or attR;
   or such that said mRNA transcript may originate from within the transposable element, and continue through one end of the transposable element, either attL or attR, and continue through target DNA;
   wherein the resulting mRNA transcript contains at least one open reading frame for translation into protein, said open reading frame encompassing nucleic acid sequences transcribed from both within the target DNA and from within the transposable element, such that the open reading frame is translated into a protein as a single contiguous polypeptide chain.

2. A transposable element of claim 1 where the exogenous DNA insertion site is within a polylinker.

3. A transposable element of claim 1, containing an inserted exogenous DNA sequence.

4. A transposable element of claim 3, where the transcription of the exogenous DNA is under controlled regulation of a promoter, enhancer, or repressor.

5. A transposable element as in claim 1 containing a right attachment site of 50 to 62 nucleotides.

6. A transposable element of claim 1 containing a DNA insert encoding a Protein A domain which allows functional protein fusion with a target protein.

7. A transposable element comprising the DNA sequence of FIG. 14, Seq. ID. No.: 24.

8. A cell wherein a transposable element of claim 3 is integrated into the cell genome.

9. A cell as in claim 8, wherein the transposable element is integrated into an autonomously replicating DNA form.

10. A cell as in claim 9, wherein the transposable element contains a Protein A DNA sequence.

11. A plasmid for inserting exogenous DNA sequences into target DNA sequences containing a transposable element of claim 1, wherein said plasmid generates protein fusions following transposition of the transposable element into target DNA.

12. A method for generating multi-functional fusion proteins, with a transposable element of claim 1, comprising insertion of an exogenous DNA sequence of a host cell into the transposable element transposition of the transposable element into a target DNA sequence, allowing transcription, translation and protein expression to occur, detecting the presence of protein, selecting for protein expressed from the exogenous DNA insert, and screening for functional fusion proteins.

13. A method for generating an in vivo protein fusion having a desired protein activity in a target organism genome comprising inserting into a transposable element of claim 1 an exogenous DNA sequence, transposing the transposable element into a target organism genome, growing the transformed target organism in culture, isolating protein preparations, and screening for fusion protein containing the desired protein activity.

14. A method for generating an in vivo carboxy terminal translational protein fusion having a desired protein activity in a target organism genome comprising inserting within the transposable element of claim 1 an exogenous DNA sequence, such that a mRNA transcript originates from the target DNA sequence and terminates within the transposable element transposing the transposable element into a target organism genome target DNA sequence, growing the target organism in culture, isolating protein, and screening for fusion protein containing the desired protein activity.

15. A method for generating an in vivo amino terminal translational protein fusion having a desired protein activity in a target organism genome with a transposable element of claim 1, comprising inserting within the transposable element an exogenous DNA sequence such that a mRNA transcript originates from the inserted exogenous DNA sequence and terminates with the target DNA sequence, transposing the transposable element into a target organism genome target DNA sequence, growing the target organism in culture, isolating all random fusion protein, and screening for fusion protein containing the desired activity.

16. A method for generating functional fusion proteins to Protein A, with a transposable element transposition of the transposable element of claim 1, comprising insertion of an exogenous Protein A DNA sequence into the transposable element, transposing into a host cell target DNA sequence, allowing transcription, translation and expression of the Protein A transcript, detecting the presence of Protein A, and isolating the Protein A fusion protein.

17. The method of claim 16 where the functional fusion protein contains a carboxy-terminal Protein A domain fused to a second amino-terminal domain, wherein said carboxy-terminal Protein A domain is of sufficient size to retain binding activity for immunoglobulin proteins.

18. The method of claim 16 where the functional fusion protein contains an amino-terminal Protein A domain fused to a second carboxy-terminal domain.

19. The method of claim 16 where the transposable element is first transposed into a chromosomal DNA to generate a cell which contains the transposable element within its chromosomal DNA, and wherein the transposable element is capable of further transposition into another target DNA sequence.

* * * * *

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: misc_feature
      (B) LOCATION: 1..32
      (D) OTHER INFORMATION: /note= "polylinker upperstrand
          Figure 1"

(xi) SEQUENCE DESCRIPTION: SEQ ID NO:1:

GTCGCGATCG GCGGCCGCAT CGATGTCGAC GG      32

(2) INFORMATION FOR SEQ ID NO:2:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: cDNA (ix) FEATURE:
    (A) NAME/KEY: misc_feature
    (B) LOCATION: 1..33
    (D) OTHER INFORMATION: /note= "polylinker lower strand
        Figure 1"

(xi) SEQUENCE DESCRIPTION: SEQ ID NO:2:

```
GGTACCCATA TGGAATTCGG ATCCGTCGAC ATC                                33
```

(2) INFORMATION FOR SEQ ID NO:3:

(i) SEQUENCE CHARACTERISTICS:
    (A) LENGTH: 117 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: misc_feature
    (B) LOCATION: 1..117
    (D) OTHER INFORMATION: /note= "delta 65 of Figure 2"

(xi) SEQUENCE DESCRIPTION: SEQ ID NO:3:

```
GGAATTCCTG TAATGAATAA AAAGCAGTAA TTAATACATC TGTTTCATTT GAAGCGCGAA    60
AGCTAAAGTT TTCGCATTTA TCGTGAAACG CTTTCGCGTT TTTCGTGCGC CGCTTCA      117
```

(2) INFORMATION FOR SEQ ID NO:4:

(i) SEQUENCE CHARACTERISTICS:
    (A) LENGTH: 83 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: misc_feature
    (B) LOCATION: 1..83
    (D) OTHER INFORMATION: /note= "delta 66 of figure 2"

(xi) SEQUENCE DESCRIPTION: SEQ ID NO:4:

```
GGAATTCCTT TCATTTGAAG CGCGAAAGCT AAAGTTTTCG CATTTATCGT GAAACGCTTT    60
CGCGTTTTTC GTGCGCCGCT TCA                                           83
```

(2) INFORMATION FOR SEQ ID NO:5:

(i) SEQUENCE CHARACTERISTICS:
    (A) LENGTH: 71 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: misc_feature
    (B) LOCATION: 1..71
    (D) OTHER INFORMATION: /note= "delta 21 of figure 2"

(xi) SEQUENCE DESCRIPTION: SEQ ID NO:5:

```
GGAATTCCCG CGAAAGCTAA AGTTTTCGCA TTTATCGTGA AACGCTTTCG CGTTTTTCGT    60
GCGCCGCTTC A                                                        71
```

(2) INFORMATION FOR SEQ ID NO:6:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..58
        (D) OTHER INFORMATION: /note= "delta 1 of figure 2"

(xi) SEQUENCE DESCRIPTION: SEQ ID NO:6:

GGAATTCCGT TTTCGCATTT ATCGTGAAAC GCTTTCGCGT TTTTCGTGCG CCGCTTCA      58

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..18
        (D) OTHER INFORMATION: /note= "delta 104 of figure 2"

(xi) SEQUENCE DESCRIPTION: SEQ ID NO:7:

CGGAATTCCG CCGCTTCA      18

(2) INFORMATION FOR SEQ ID NO:8:

(i) SEQUENCE CHARACTERISTICS:
        (A) LENGTH: 39 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..39
        (D) OTHER INFORMATION: /note= "READING FRAME 1, FIGURE 2,
            X = STOP"

(xi) SEQUENCE DESCRIPTION: SEQ ID NO:8:

Gly Ile Pro Val Met Asn Lys Lys Gln Xaa Leu Ile His Leu Phe His
1              5                   10                 15

Leu Lys Arg Glu Ser Xaa Ser Phe Arg Ile Tyr Arg Glu Thr Leu Ser
        20                   25                 30

Arg Phe Ser Cys Ala Ala Ser
        35

(2) INFORMATION FOR SEQ ID NO:9:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide (B) LOCATION: 1..38
            (D) OTHER INFORMATION: /note= "READING FRAME 2, FIGURE 2,
                X = STOP"

(xi) SEQUENCE DESCRIPTION: SEQ ID NO:9:

Glu Phe Leu Xaa Xaa Ile Lys Ser Ser Asn Xaa Tyr Ile Cys Phe Ile
1               5                   10                  15

Xaa Ser Ala Lys Ala Lys Val Phe Ala Phe Ile Val Lys Arg Phe Arg
                20                  25                  30

Val Phe Arg Ala Pro Leu
            35

(2) INFORMATION FOR SEQ ID NO:10:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..38
        (D) OTHER INFORMATION: /note= "READING FRAME 3, FIGURE 2,
            X = STOP"

(xi) SEQUENCE DESCRIPTION: SEQ ID NO:10:

Asn Ser Cys Asn Glu Xaa Lys Ala Val Ile Asn Thr Ser Val Ser Phe
1               5                   10                  15

Glu Ala Arg Lys Leu Lys Phe Ser His Leu Ser Xaa Asn Ala Phe Ala
                20                  25                  30

Phe Phe Val Arg Arg Phe
            35

(2) INFORMATION FOR SEQ ID NO:11:

(i) SEQUENCE CHARACTERISTICS:
        (A) LENGTH: 39 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..39
        (D) OTHER INFORMATION: /note= "READING FRAME 4, FIGURE 2,
            X = STOP"

(xi) SEQUENCE DESCRIPTION: SEQ ID NO:11:

Ser Asn Arg Tyr His Ile Phe Leu Leu Leu Xaa Tyr Met Gln Lys Met
1               5                   10                  15

Gln Leu Ala Phe Ala Leu Thr Lys Ala Asn Ile Thr Phe Arg Lys Arg
                20                  25                  30

Thr Lys Arg Ala Gly Ser Xaa
            35

(2) INFORMATION FOR SEQ ID NO:12:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: peptide (ix) FEATURE:
              (A) NAME/KEY: Peptide
              (B) LOCATION: 1..38
              (D) OTHER INFORMATION: /note= "READING FRAME 5, FIGURE 2,
                  X   STOP"

(xi) SEQUENCE DESCRIPTION: SEQ ID NO:12:

Ile Gly Thr Ile Phe Leu Phe Cys Tyr Asn Ile Cys Arg Asn Xaa Lys
1               5                   10                  15

Phe Arg Ser Leu Xaa Leu Lys Arg Met Xaa Arg Ser Val Ser Glu Arg
                20                  25                  30

Lys Glu His Ala Ala Glu
            35

(2) INFORMATION FOR SEQ ID NO:13:

(i) SEQUENCE CHARACTERISTICS:
              (A) LENGTH: 38 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Peptide
              (B) LOCATION: 1..38
              (D) OTHER INFORMATION: /note= "READING FRAME 6, FIGURE 2,
                  X = STOP"

(xi) SEQUENCE DESCRIPTION: SEQ ID NO:13:

Phe Glu Gln Leu Ser Tyr Phe Ala Thr Ile Leu Val Asp Thr Glu Asn
1               5                   10                  15

Ser Ala Arg Phe Ser Phe Asn Glu Cys Lys Asp His Phe Ala Lys Ala
                20                  25                  30

Asn Lys Thr Arg Arg Lys
            35

(2) INFORMATION FOR SEQ ID NO:14:

(i) SEQUENCE CHARACTERISTICS:
              (A) LENGTH: 68 base pairs
              (B) TYPE: nucleic acid
              (C) STRANDEDNESS: single
              (D) TOPOLOGY: linear (ii) MOLECULE TYPE: cDNA (ix) FEATURE:
              (A) NAME/KEY: misc_feature
              (B) LOCATION: 1..68
              (D) OTHER INFORMATION: /note= "pIVP315 polylinker, Figure
                  3"

(xi) SEQUENCE DESCRIPTION: SEQ ID NO:14:

GGAATTGGTA CCCATATGGA ATTCGGATCC GTCGACATCG ATGCGGCCGC CGATCGCGAC      60

AATTCCGT                                                              68

(2) INFORMATION FOR SEQ ID NO:15:

(i) SEQUENCE CHARACTERISTICS:
              (A) LENGTH: 23 amino acids
              (B) TYPE: amino acid
              (C) STRANDEDNESS: single
              (D) TOPOLOGY: linear (ii) MOLECULE TYPE: peptide (ix) FEATURE:
    (A) NAME/KEY: Peptide
    (B) LOCATION: 1..23
    (D) OTHER INFORMATION: /note= "READING FRAME 1, FIGURE 3,
        ORF"

(xi) SEQUENCE DESCRIPTION: SEQ ID NO:15:

Gly Ile Gly Thr His Met Glu Phe Gly Ser Val Asp Ile Asp Ala Ala
1            5                    10                15

Ala Asp Arg Asp Asn Ser Val
        20

(2) INFORMATION FOR SEQ ID NO:16:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..23
        (D) OTHER INFORMATION: /note= "READING FRAME 2, FIGURE 3,
            NOT OPEN READING FRAME"

(xi) SEQUENCE DESCRIPTION: SEQ ID NO:16:

Glu Leu Val Pro Ile Trp Asn Ser Asp Pro Ser Thr Ser Met Arg Pro
1            5                    10                15

Pro Ile Ala Thr Ile Pro Phe
        20

(2) INFORMATION FOR SEQ ID NO:17:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..22
        (D) OTHER INFORMATION: /note= "READING FRAME 3, FIGURE 3,
            ORF"

(xi) SEQUENCE DESCRIPTION: SEQ ID NO:17:

Asn Trp Tyr Pro Tyr Gly Ile Arg Ile Arg Arg His Arg Cys Gly Arg
1            5                    10                15

Arg Ser Arg Gln Phe Arg
        20

(2) INFORMATION FOR SEQ ID NO:18:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..22
        (D) OTHER INFORMATION: /note= "READING FRAME 4, FIGURE 3,

NOT OPEN READING FRAME"

(xi) SEQUENCE DESCRIPTION: SEQ ID NO:18:

Thr Glu Leu Ser Arg Ser Ala Ala Ala Ser Met Ser Thr Asp Pro Asn
1               5                   10                  15

Ser Ile Trp Val Pro Ile
            20

(2) INFORMATION FOR SEQ ID NO:19:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..22
        (D) OTHER INFORMATION: /note= "READING FRAME 5, FIGURE 3,
            NOT OPEN READING FRAME"

(xi) SEQUENCE DESCRIPTION: SEQ ID NO:19:

Arg Asn Cys Arg Asp Arg Arg Pro His Arg Cys Arg Arg Ile Arg Ile
1               5                   10                  15

Pro Tyr Gly Tyr Gln Phe
            20

(2) INFORMATION FOR SEQ ID NO:20:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..22
        (D) OTHER INFORMATION: /note= "READING FRAME 6, FIGURE 3,
            ORF"

(xi) SEQUENCE DESCRIPTION: SEQ ID NO:20:

Gly Ile Val Ala Ile Gly Gly Arg Ile Asp Val Asp Gly Ser Glu Phe
1               5                   10                  15

His Met Gly Thr Asn Ser
            20

(2) INFORMATION FOR SEQ ID NO:21:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..45
        (D) OTHER INFORMATION: /note= "POLYLINKER SEQUENCE, FIGURE
            11"

(xi) SEQUENCE DESCRIPTION: SEQ ID NO:21:

GAATTCGAGC TCGGTACCCG GGGATCCGTC GACCTGCAGA AGCTT                    45

(2) INFORMATION FOR SEQ ID NO:22:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..66
        (D) OTHER INFORMATION: /note= "MALPI-L, FIGURE 13"

(xi) SEQUENCE DESCRIPTION: SEQ ID NO:22:

```
GGGGGTACCG CCCGCCTAAT GAGCGGGCTT TTTTTTCCGA CACCATCGAA TGGCGCAAAA     60

CCTTTC                                                                66
```

(2) INFORMATION FOR SEQ ID NO:23:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..37
        (D) OTHER INFORMATION: /note= "MALPI-R, FIGURE 13"

(xi) SEQUENCE DESCRIPTION: SEQ ID NO:23:

```
GGGGATCCAT AATCTATGGT CCTTGTTGGT GAAGTGC                              37
```

(2) INFORMATION FOR SEQ ID NO:24:

(i) SEQUENCE CHARACTERISTICS:
        (A) LENGTH: 7003 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: misc_feature
        (B) LOCATION: 1..7003
        (D) OTHER INFORMATION: /note= "MueII315, Figure 14"

(xi) SEQUENCE DESCRIPTION: SEQ ID NO:24:

```
TGTATTGATT CACTTGAAGT ACGAAAAAAA CCGGGAGGAC ATTGGATTAT TCGGGATCTG     60

ATGGGATTAG ATTTGGTGGG GCTTGCAAGC CTGTAGTGCA AATTTTAGTC GTTAATCAAT    120

GAAACGCGAA AGATAGTAAA AAATTGCTTT TGTTTCATTG AAAATACGAA AAACAAAAAC    180

ACTGCAAATC ATTTCAATAA CAGCTTCAAA AAACGTTCAA AACCGATAAC AACCAAGCTG    240

TCACCAAATG ACTCATATCA CAAATCAGCT TATGCCGTTT AGGTATGTTA CATGTGTGAT    300

TATGTGAGGT GAAGTATGTT TTAGCTGGTT CATGGTTGTT ATACGGCTTT TTTTACCTCC    360

GTGGGTTCCT GTGAAGGTAC TACAACACCT TCCTGTTCAT GAATCCCATA CTTTGACAAA    420

ATCTCTTTGC GTTTTTCTTC AGGTAATGCA TCTAGCATCA TCAACGTCTG AATACTTTGC    480

TGTGAAAATC CTATAAAGCT GTAAAGTTTC TGTTCATTAA ATACAAGAGG CATTAACGCC    540

AACAACCCCC CTTTACTTAA AAGTTTCAGT GCCTTGCGTG CTTCATCTGG TTCCAGCTCT    600
```

```
TCAATCATAT TGATTAAGGT TGTGGTTAAT TTGTTTATCA GTTCCGAAGA ATCCTGTTTC    660

TCATTGGCTT GAGCACCAGT ATCCGGTGTG GATAACCCCA AGTGCGCAAT AACTTGCTCT    720

CGTTCTTTGG TGGGCATCGA CATCACATCG TATTCAACAG CTTTCCCCCC CTTGACACCT    780

TCCTTTTTTT GCTTCGTCCA GCCTTGAACA TTTGCTCGAT AGTGAACACC AGCAACAGAT    840

CCAGGCATAC CATCAGCAGC CATAATTTCT TGCGGCGAAC ACCAAATTGA CTTTTCAGTA    900

TTATTCTTTT CTATAAAGTT ACTTTTCAAA ATTTAAACTC CTTATTTATC AACGCGTTAA    960

TCAGTAATCA AAGGAATTTA CCAAAAAGCA GCTTTACATT AAGCTTTTCA GTAATTATCT   1020

TTTTAGTAAG CTAGCTAAGT TTTTACACTT AGTTAAATTG CTAACTTTAT AGATTACAAA   1080

ACTTAGGAGG GTTTTTAAAT GTGTTCCAAC GAAAAGGCCC GTGATTGGCA TCGTGCGGAT   1140

GTGATTGCGG GACTTAAGAA AAGAAAGCTC TCTTTATCAG CTCTTTCCCG GCAGTTTGGT   1200

TATGCGCCAA CTACATTAGC TAATGCGCTA GAACGACACT GGCCAAAGGG TGAGCAGATT   1260

ATTGCTAACG CCTTAGAAAC TAAACCGGAA GTAATCTGGC CTAGCCGATA TCAAGCAGGT   1320

GAATAACATG GAACTTTGGG TATCACCGAA AGAGTGTGCG AATCTTCCTG GTTTGCCGAA   1380

AACATCGGCT GGTGTGATTT ATGTTGCTAA AAAGCAAGGA TGGCAAAACC GCACTAGAGC   1440

AGGTGTCAAA GGTGGTAAAG CAATTGAATA CAATGCGAAC TCTTTACCTG TTGAAGCGAA   1500

AGCGGCGTTA TTGCTGAGAC AAGGAGAGAT TGAAACAAGC CTGGGGTATT TTGAAATCGC   1560

CCGCCCCACG CTGGAAGCCC ATGATTATGA TCGTGAGGCA CTGTGGAGCA AATGGGATAA   1620

CGCCAGCGAT TCCCAGCGCA GACTTGCTGA AAAATGGTTG CCTGCGGTTC AGGCTGCAGA   1680

CGAAATGCTG AACCAGGGGA TTTCAACGAA AACGGCTTTT GCGACCGTTG CAGGGCATTA   1740

CCAGGTCAGC GCATCCACTT TGCGGGACAA GTATTACCAG GTACAGAAGT TTGCGAAGCC   1800

TGACTGGGCG GCTGCACTTG TTGATGGACG TGGAGCATCC CGTCGCAATG TTCACAAAAG   1860

TGAATTTGAC GAGGATGCCT GGCAGTTTCT GATTGCAGAT TATCTGCGAC CGGAAAAACC   1920

CGCTTTCCGC AAATGTTATG AGCGTCTGGA ACTGGCAGCC CGCGAGCATG GCTGGAGTAT   1980

TCCCTCCCGT GCCACGGCCT TTCGCCGGAT TCAGCAACTG GACGAGGCAA TGGTTGTTGC   2040

CTGTCGTGAA GGTGAACATG CACTGATGCA TCTGATACCG GCACAGCAGC GAACTGTGGA   2100

ACACCTGGAC GCCATGCAGT GGATCAACGG CGACGGTTAT CTGCATAACG TCTTTGTACG   2160

CTGGTTTAAC GGTGATGTGA TCCGTCCGAA AACATGGTTC TGGCAGGATG TGAAAACCCG   2220

AAAAATTCTG GGCTGGCGCT GCGATGTGAG CGAGAACATT GATTCAATTC GCCTCTCGTT   2280

CATGGATGTT GTGACTCGCT ACGGTATCCC GGAGGATTTT CACATCACCA TTGATAACAC   2340

CCGTGGTGCT GCGAATAAAT GGCTGACGGG AGGCGCGCCC AATCGCTACC GCTTTAAGGT   2400

AAAAGAGGAC GATCCAAAAG GACTGTTTTT ACTGATGGGG GCGAAAATGC ACTGGACAAG   2460

CGTTGTTGCC GGTAAAGGCT GGGGCCAGGC AAAACCTGTT GAACGTGCTT TCGGTGTTGG   2520

TGGGCTTGAG GAATACGTTG ATAAGCATTC GGCACTGGCT GGCGCATATA CGGGGCCAAA   2580

TCCGCAGGCA AAACCTGATA ACTATGGCGA CCGCGCTGTT GATGCAGAGC TGTTTCTGAA   2640

AACCCTTGCC GAAGGTGTGG CGATGTTCAA TGCCAGAACA GGCCGTGAAA CAGAAATGTG   2700

CGGGGGCAAA CTCTCGTTTG ATGATGTTTT CGAGCGTGAA TACGCCAGAA CGATTGTGCG   2760

TAAGCCAACC GAAGAACAAA AACGGATGCT GTTACTGCCT GCCGAGGCGG TGAACGTTTC   2820

ACGCAAAGGC GCGTTTACGC TTAAAGTTGG CGGCTCCCTT AAAGGCGCGA AAACGTTTA    2880

TTACAACATG GCATTAATGA ATGCCGGCGT GAAAAAAGTT GTGGTCAGGT TGATCCGCA    2940

GCAGCTACAC AGCACGGTTT ATTGCTACAC CCTGGACGGT CGGTTTATCT GTGAAGCGGA   3000
```

```
ATGTCTGGCA CCTGTTGCAT TTAATGATGC TGCGGCAGGC CGTGAATATC GCCGCCGCCA    3060

GAAACAACTG AAATCTGCGA CGAAAGCAGC CATTAAGGCG CAGAAACAAA TGGACGCGCT    3120

GGAAGTTGCT GAACTGCTGC CGCAGATAGC CGAACCAGCA GCACCAGAAT CACGAATTGT    3180

TGGTATTTTC CGGCCTTCCG GTAATACGGA ACGGGTGAAG AATCAGGAGC GTGATGATGA    3240

ATACGAAACT GAGCGTGATG AATATCTGAA TCATTCGCTG GATATTCTGG AACAGAACAG    3300

ACGTAAAAAA GCCATTTAAT TAACGTTTAA ACAAAATTTA ATTACGAGGT TATTCAGATG    3360

AATATTTCCG ATATTCGCGC AGGACTGCGC ACGCTTGTAG AAAATGAAGA AACCACCTTT    3420

AAACAAATTG CTCTTGAGAG CGGGCTTTCT ACCGGAACTA TCAGTAGTTT TATCAATGAT    3480

AAGTACAACG GGGATAACGA GCGTGTTTCA CAAATGCTGC AACGCTGGCT GGAAAAATAT    3540

CATGCAGTGG CAGAACTACC TGAACCGCCC CGCTTTGTGG AAACGCAGAC GGTAAAACAA    3600

ATCTGGACAA GTATGCGTTT TGCCAGCCTG ACTGAAAGTA TTGCTGTTGT ATGTGGCAAT    3660

CCTGGTGTGG GCAAAACCGA AGCGGCCCGT GAATATCGCC GCACCAATAA CAATGTCTGG    3720

ATGATCACCA TTACGCCATC CTGTGCCAGC GTTCTGGAAT GTCTTACTGA ACTGGCGTTT    3780

GAGCTGGGAA TGAATGACGC ACCACGCCGT AAAGGGCCGC TCTCCCGCGC CCTGCGACGT    3840

CGCCTTGAAG GTACACAGGG GCTGGTTATC ATCGACGAAG CTGATCATCT TGGTGCCGAA    3900

GTTCTGGAAG AACTCCGCCT GTTACAGGAA TCAACCCGTA TTGGCCTTGT GCTGATGGGA    3960

AATCACCGGG TTTATTCAAA TATGACGGGG GGTAACAGAA CGGTTGAATT TGCCCGTCTG    4020

TTTTCCCGTA TTGCAAAGCG CACTGCAATT AATAAAACCA AAAAGCCGA TGTAAAAGCT     4080

ATTGCGGATG CCTGGCAGAT TAACGGCGAA AAAGAACTGG AGTTATTACA GCAGATTGCG    4140

CAGAAACCAG GTGCGCTTCG CATTCTGAAT CATTCACTTC GCCTTGCAGC CATGACGGCT    4200

CACGGTAAAG GTGAGCGTGT TAACGAAGAT TATCTGCGTC AGGCTTTCCG TGAATTAGAC    4260

CTGGACGTTG ATATTTCAAC GCTGCTGCGT AATTAAGAGG GAGAAGAAAT TATGATGGCC    4320

CCGAAATATA AAAATGGCAA CGGATGCGCA GAACTGGTTA CAGGCGCGGC TGACTCTTAT    4380

ACACAAGTAG CGTCCTGAAC GGAACCTTTC CCGTTTTCCA GGATCTGACT TCCATGTGAC    4440

CTCCTAACAT GGTAACGTTC ATGATAACTT CTGCTCTTCA TCGTGCGCGC GACTGGGCTA    4500

AATCTGTGTT CTCTTGCCGG GCGCTGGGTG ATCCTCGCCG TACTGCCCGC TTGGTTAACG    4560

TCGCCGCCCA ATTGGCAAAA TATTCTGGTA AATCAATAAC CATCTCATCA GAGGGTAGTG    4620

AAGCCATGCA GGAAGGCGCT TACCGATTTT ACCGCAATCC CAACGTTTCT GCCGAGGCGA    4680

TCAGAAAGGC TGGCGCCATG CAAACAGTCA AGTTGGCTCA GGAGTTTCCC GAACTGCTGG    4740

CCATTGAGGA CACCACCTCT TTGAGTTATC GCCACCAGGT CGCCGAAGAG CTTGGCAAGC    4800

TGGGCTCTAT TCAGGATAAA TCCCGCGGAT GGTGGGTTCA CTCGGTTCTC TTGCTCGAGG    4860

CCACCACATT CCGCACCGTA GGATTACTGC ATCAGGAGTG GTGGATGCGC CCGGATGACC    4920

CTGCCGATGC GGATGAAAAG AAGAGTGGCA AATGGCTGGC AGCGGCCGCA ACTAGCCGGT    4980

TACGCATGGG CAGCATGATG AGCAACGTGA TTGCGGTCTG TGACCGCGAA GCCGATATTC    5040

ATGCTTATCT GCAGGACAGG CTGGCGCATA CCGAGCGCTT CGTGGTGCGC TCCAAGCACC    5100

CACGCAAGGA CGTAGAGTCT GGGTTGTATC TGATCGACCA TCTGAAGAAC CAACCGGAGT    5160

TGGTTGGCTA TCAGATCAGC ATTCCGCAAA AGGGCGTGGT GGATAAACGC GGTAAACGTA    5220

AAAATCGACC AGCCCGCAAG GCGAGCTTGA GCCTGCGCAG TGGGCGCATC ACGCTAAAAC    5280

AGGGGAATAT CACGCTCAAC GCGGTGCTGG CCGAGGAGAT TAACCCGCCC AAGGGTGAGA    5340

CCCCGTTGAA ATGGTTGTTG CTGACGCGCG AACCGGTCGA GTCGCTAGCC CAAGCCTTGC    5400
```

```
GCGTCATCGA CATTTATACC CATCGCTGGC GGATCGAGGA GTTCCATAAG GCATGGAAAA    5460

CCGGAGCAGG AGCCGAGAGG CAACGCATGG AGGAGCCGGA TAATCTGGAG CGGATGGTCT    5520

CGATCCTCTC GTTTGTTGCG GTCAGGCTGT TACAGCTCAG AGAAAGCTTC ACGCTGCCGC    5580

AAGCACTCAG GGCGCAAGGG CTGCTAAAGG AAGCGGAACA CGTAGAAAGC CAGTCCGCAG    5640

AAACGGTGCT GACCCCGGAT GAATGTCAGC TACTGGGCTA TCTGGACAAG GGAAAACGCA    5700

AGCGCAAAGA GAAAGCAGGT AGCTTGCAGT GGGCTTACAT GGCGATAGCT AGACTGGGCG    5760

GTTTTATGGA CAGCAAGCGA ACCGGAATTG CCAGCTGGGG CGCCCTCTGG TAAGGTTGGG    5820

AAGCCCTGCA AAGTAAACTG GATGGCTTTC TTGCCGCCAA GGATCTGATG GCGCAGGGGA    5880

TCAAGATCTG ATCAAGAGAC AGGATGAGGA TCGTTTCGCA TGATTGAACA AGATGGATTG    5940

CACGCAGGTT CTCCGGCCGC TTGGGTGGAG AGGCTATTCG GCTATGACTG GGCACAACAG    6000

ACAATCGGCT GCTCTGATGC CGCCGTGTTC CGGCTGTCAG CGCAGGGGCG CCCGGTTCTT    6060

TTTGTCAAGA CCGACCTGTC CGGTGCCCTG AATGAACTGC AGGACGAGGC AGCGCGGCTA    6120

TCGTGGCTGG CCACGACGGG CGTTCCTTGC GCAGCTGTGC TCGACGTGGT CACTGAAGCG    6180

GGAAGGGACT GGCTGCTATT GGGCGAAGTG CCGGGGCAGG ATCTCCTGTC ATCTCACCTT    6240

GCTCCTGCCG AGAAAGTATC CATCATGGCT GATGCAATGC GGCGGCTGCA TACGCTTGAT    6300

CCGGCTACCT GCCCATTCGA CCACCAAGCG AAACATCGCA TCGAGCGAGC ACGTACTCGG    6360

ATGGAAGCCG GTCTTGTCGA TCAGGATGAT CTGGACGAAG AGCATCAGGG GCTCGCGCCA    6420

GCCGAACTGT TCGCCAGGCT CAAGGCGCGC ATGCCCGACG GCGAGGATCT CGTCGTGACC    6480

CATGGCGATG CCTGCTTGCC GAATATCATG GTGGAAAATG GCCGCTTTTC TGGATTCATC    6540

GACTGTGGCC GGCTGGGTCT GGCGGACCGC TATCAGGACA TAGCGTTGGC TACCCGTGAT    6600

ATTGCTGAAG AGCTTGGCGG CGAATGGGCT GACCGCTTCC TCGTGCTTTA CGGTATCGCC    6660

GCTCCCGATT CGCAGCGCAT CGCCTTCTAT CGCCTTCTTG ACGAGTTCTT CTGAGCGGGA    6720

CTCTGGGGTT CGAAATGACC GACCAAGCGA CGCCCAACCT GCCATCACGA GATTTCGATT    6780

CCACCGCCGC CTTCTATGAA AGGTTGGGCT TCGGAATCGT TTTCCGGGAC GCCGGCTGGA    6840

TGATCCTCCA GCGCGGGGAT CTCATGCTGG AGTTCTTCGC CCACCCCGGA ATTGGTACCC    6900

ATATGGAATT CGGATCCGTC GACATCGATG CGGCCGCCGA TCGCGACAAT TCCGTTTTCG    6960

CATTTATCGT GAAACGCTTT CGCGTTTTTC GTGCGCCGCT TCA                     7003
```